(12) United States Patent
Shturman

(10) Patent No.: US 8,496,678 B2
(45) Date of Patent: Jul. 30, 2013

(54) ROTATIONAL DEVICE WITH INFLATABLE SUPPORT ELEMENTS AND TORQUE TRANSMITTING MEMBRANE

(75) Inventor: Leonid Shturman, Nyon (CH)

(73) Assignee: Cardio Flow, inc., Long Lake, MN (US)

( * ) Notice: Subject to any disclaimer, the term of this patent is extended or adjusted under 35 U.S.C. 154(b) by 0 days.

(21) Appl. No.: 13/411,817

(22) Filed: Mar. 5, 2012

(65) Prior Publication Data

US 2012/0165846 A1   Jun. 28, 2012

Related U.S. Application Data

(63) Continuation of application No. 12/373,445, filed as application No. PCT/EP2007/056516 on Jun. 28, 2007, now Pat. No. 8,142,458.

(30) Foreign Application Priority Data

Jul. 13, 2006  (GB) .................................. 0613981.0

(51) Int. Cl.
   *A61B 17/22*   (2006.01)
(52) U.S. Cl.
   USPC .......................................................... 606/159
(58) Field of Classification Search
   None
   See application file for complete search history.

(56) References Cited

U.S. PATENT DOCUMENTS

| | | |
|---|---|---|
| 4,646,736 A | 3/1987 | Auth |
| 4,870,953 A | 10/1989 | DonMicheal et al. |
| 4,990,134 A | 2/1991 | Auth et al. |
| 5,242,460 A | 9/1993 | Klein et al. |
| 5,250,060 A | 10/1993 | Carbo et al. |
| 5,273,526 A | 12/1993 | Dance |
| 5,314,438 A | 5/1994 | Shturman |
| 5,370,653 A | 12/1994 | Cragg |
| 5,584,843 A | 12/1996 | Wulfman et al. |
| 5,681,336 A | 10/1997 | Clement et al. |
| 5,843,103 A | 12/1998 | Wulfman |
| 5,868,708 A | 2/1999 | Hart et al. |
| 6,096,054 A | 8/2000 | Wyzgala et al. |
| 6,132,444 A | 10/2000 | Shturman et al. |
| 6,146,395 A | 11/2000 | Kanz et al. |
| 6,416,526 B1 | 7/2002 | Wyzgala et al. |

(Continued)

FOREIGN PATENT DOCUMENTS

| | | |
|---|---|---|
| WO | WO98/50101 | 11/1998 |
| WO | WO99/44513 | 9/1999 |
| WO | WO2006/126175 | 11/2006 |
| WO | WO2006/126176 | 11/2006 |

OTHER PUBLICATIONS

International Search Report corresponding to Int'l Application No. PCT/EP2007/056516, dated Oct. 4, 2007.

*Primary Examiner* — Ryan Severson
*Assistant Examiner* — David Eastwood
(74) *Attorney, Agent, or Firm* — Fish & Richardson P.C.

(57) ABSTRACT

A rotational atherectomy device for removing a stenotic tissue from a vessel of a patient is disclosed. The device comprises a rotatable, flexible, hollow drive shaft having a fluid impermeable wall defining a lumen of the drive shaft, an abrasive element mounted to a distal end portion of the drive shaft proximal to and spaced away from a distal support element formed at a distal end of the drive shaft. The distal support element is inflatable by pressurized fluid which flows in an antegrade direction through said lumen of the drive shaft and is least partially re-directed into the distal fluid inflatable support element. The distal fluid inflatable support element has an outer wall comprising an outflow opening.

20 Claims, 36 Drawing Sheets

U.S. PATENT DOCUMENTS

| | | |
|---|---|---|
| 6,485,500 B1 | 11/2002 | Kokish et al. |
| 6,685,718 B1 | 2/2004 | Wyzgala et al. |
| 6,955,661 B1 | 10/2005 | Herweck et al. |
| 2002/0007190 A1 | 1/2002 | Wulflman et al. |
| 2002/0082547 A1 | 6/2002 | Deniega et al. |
| 2002/0099367 A1 | 7/2002 | Guo et al. |
| 2003/0199889 A1 | 10/2003 | Kanz et al. |
| 2004/0098014 A1 | 5/2004 | Flugelman et al. |
| 2004/0158270 A1 | 8/2004 | Wyzgala et al. |
| 2005/0154416 A1 | 7/2005 | Herweck et al. |
| 2005/0209615 A1 | 9/2005 | Prudnikov et al. |
| 2005/0240146 A1 | 10/2005 | Nash et al. |
| 2005/0256461 A1 | 11/2005 | DiFiore et al. |

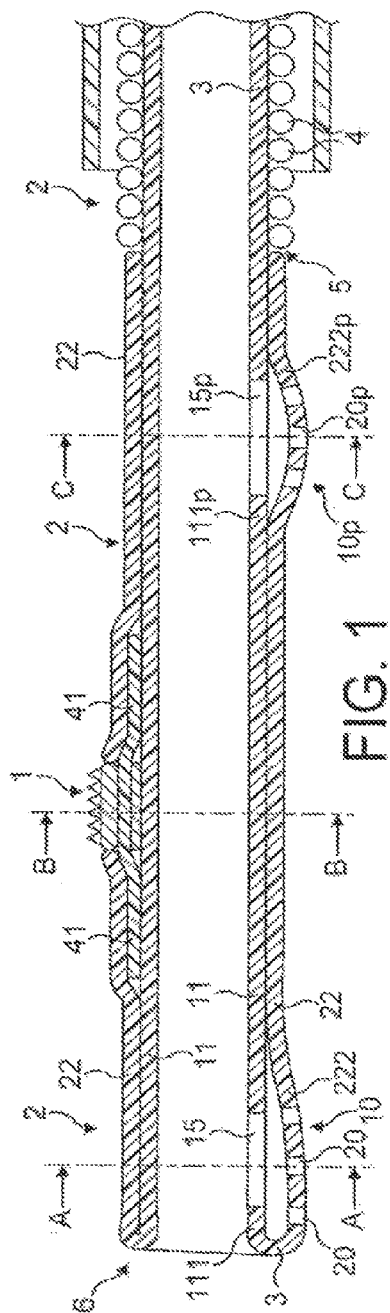
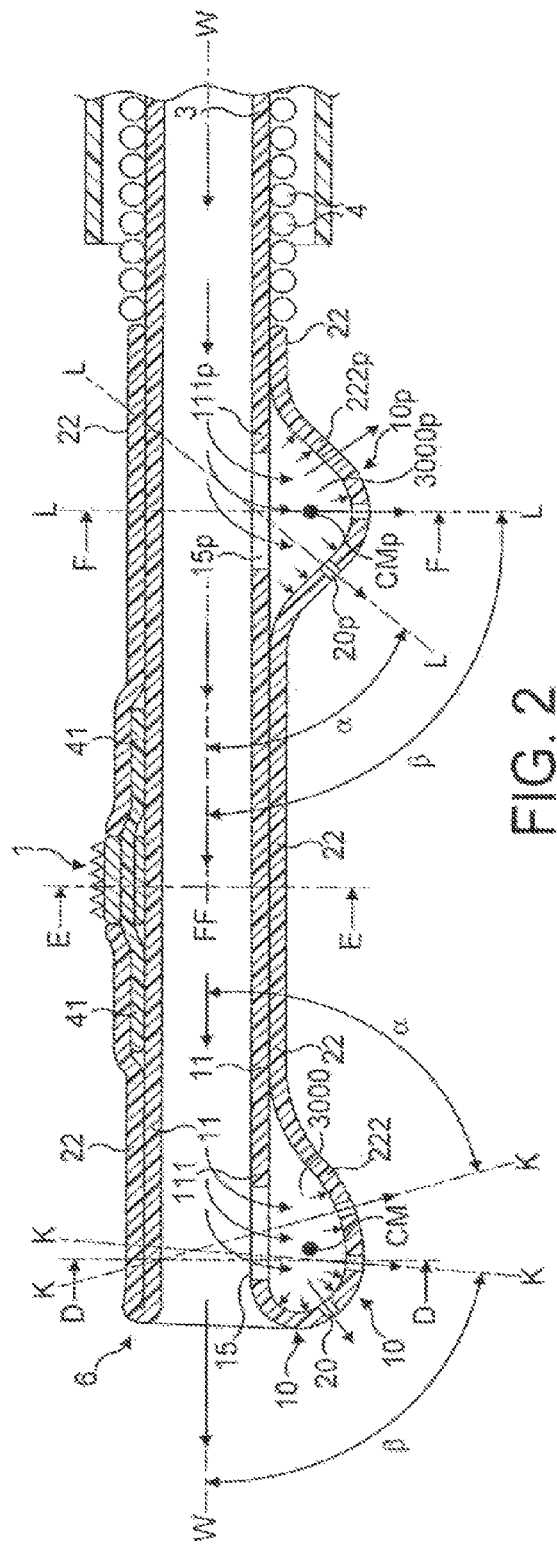

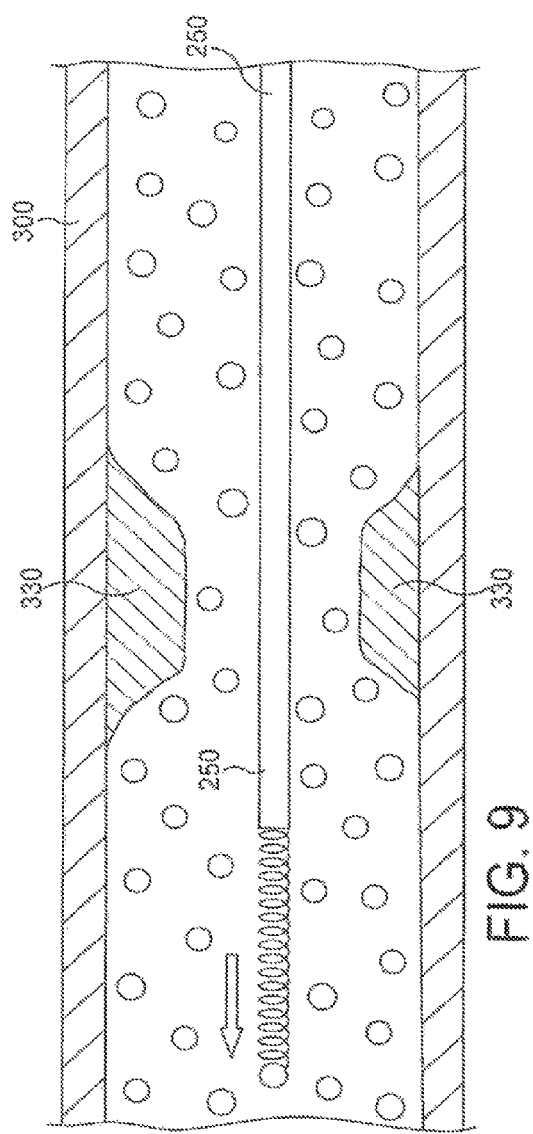
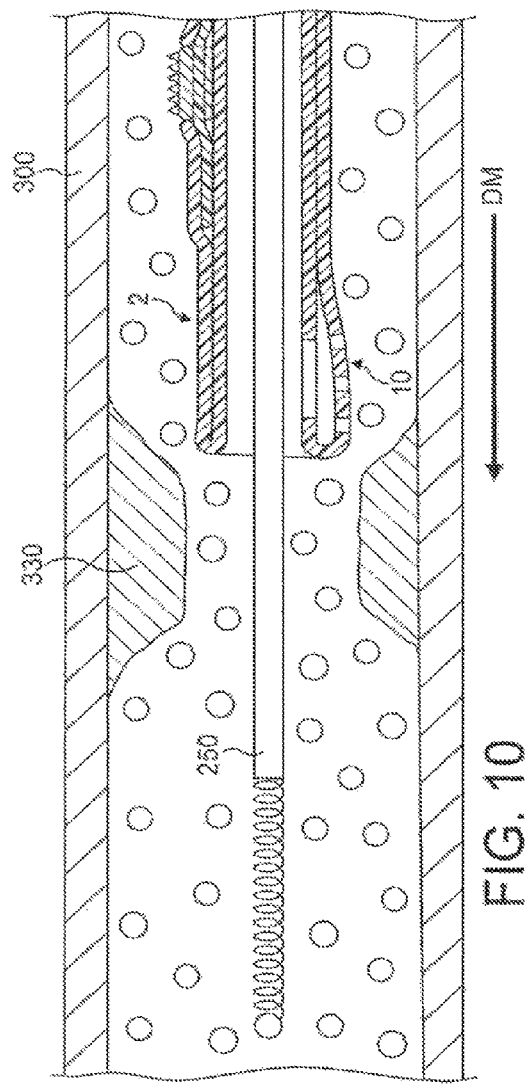
FIG. 9
FIG. 10

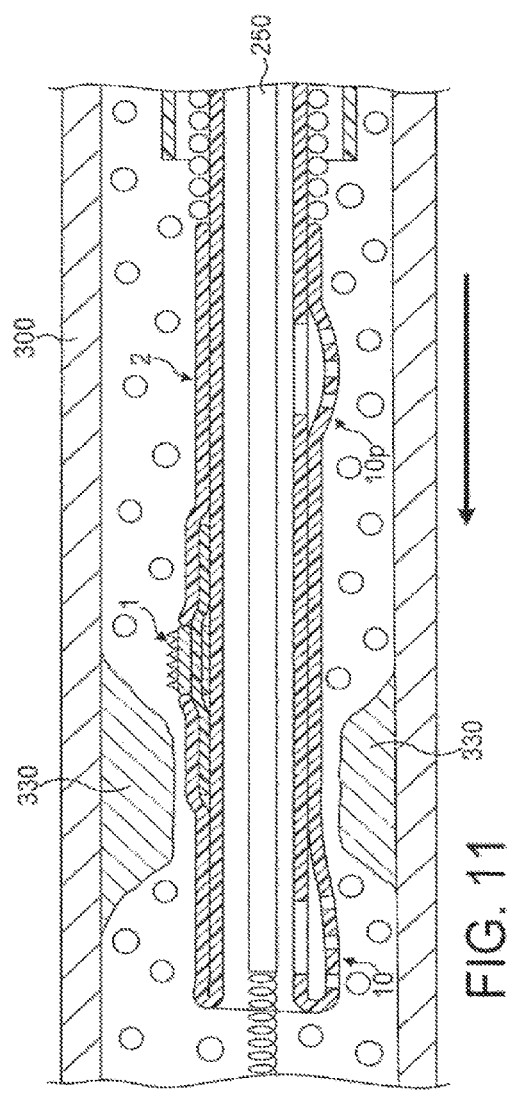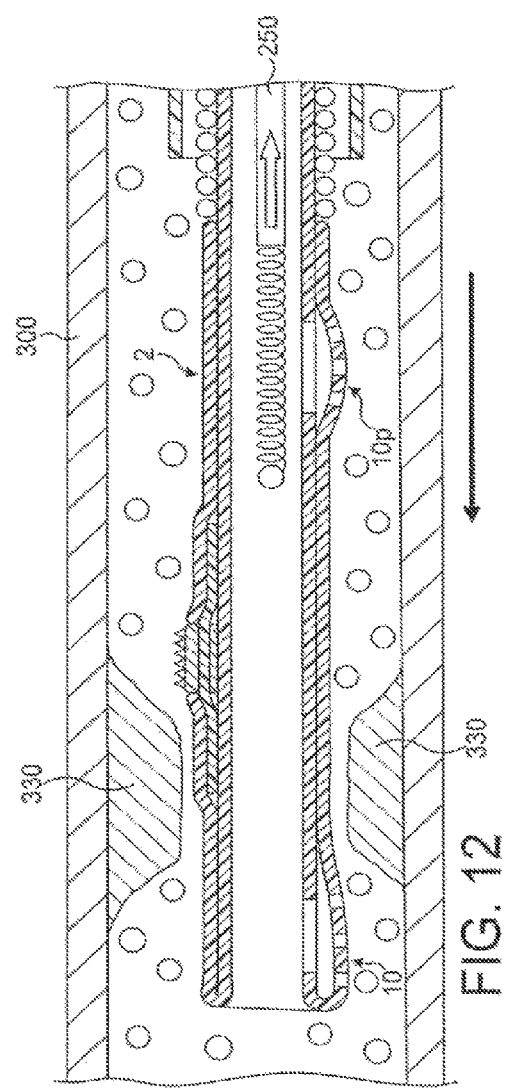

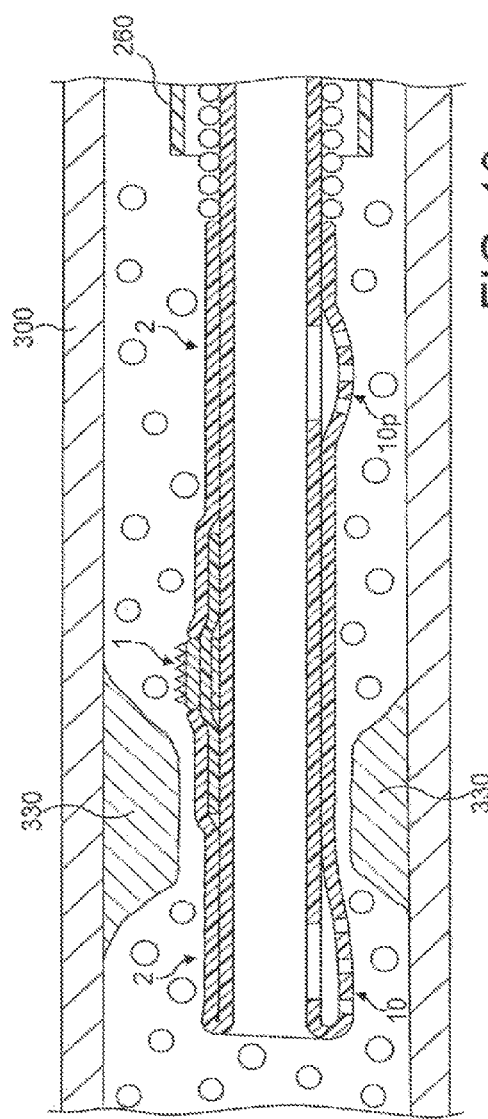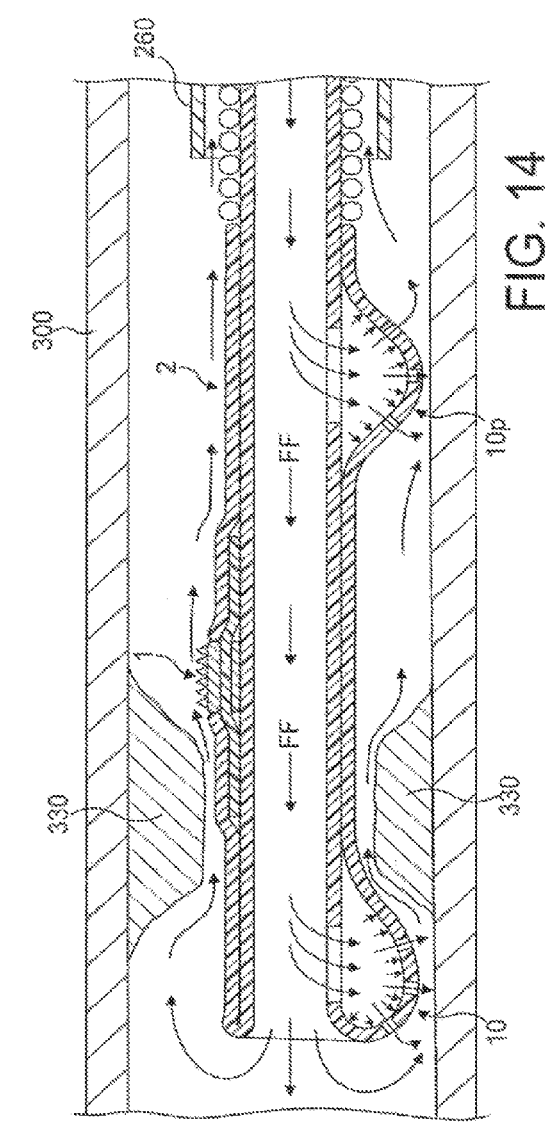
FIG. 13
FIG. 14

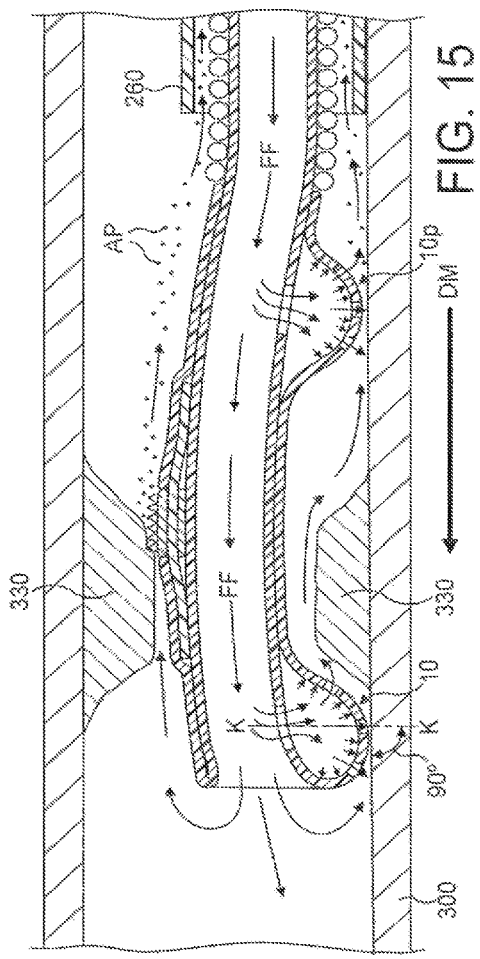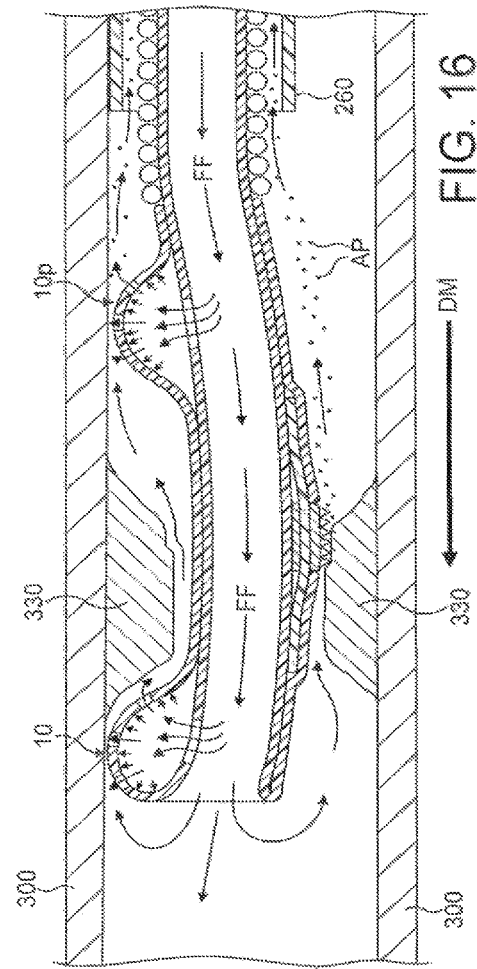

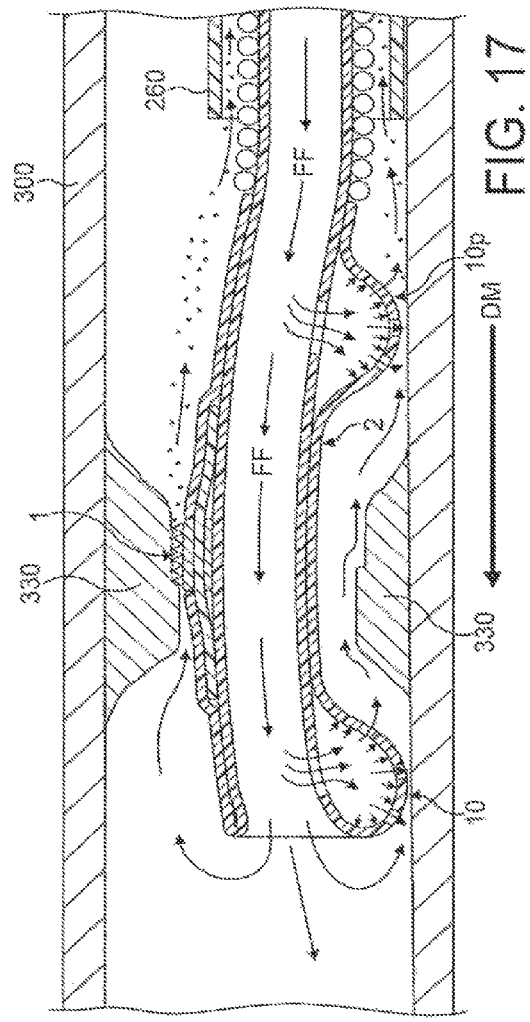
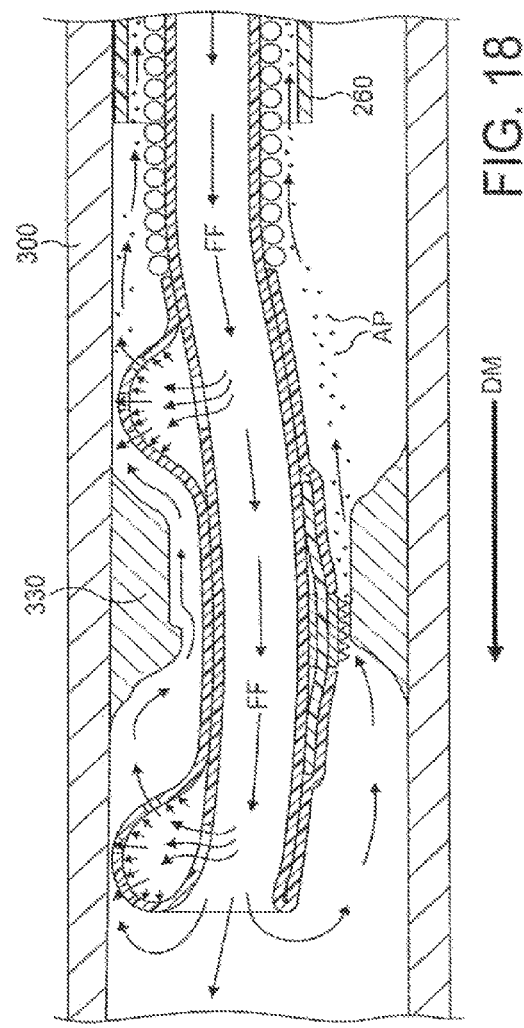

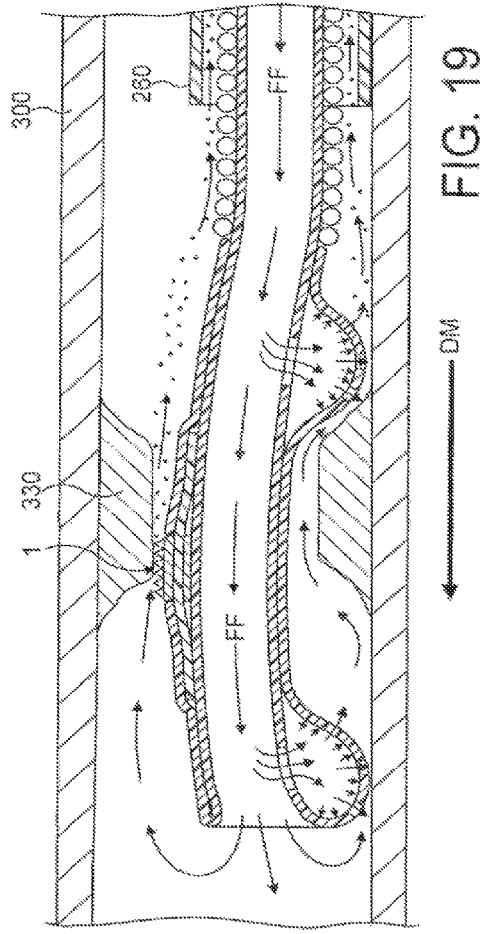
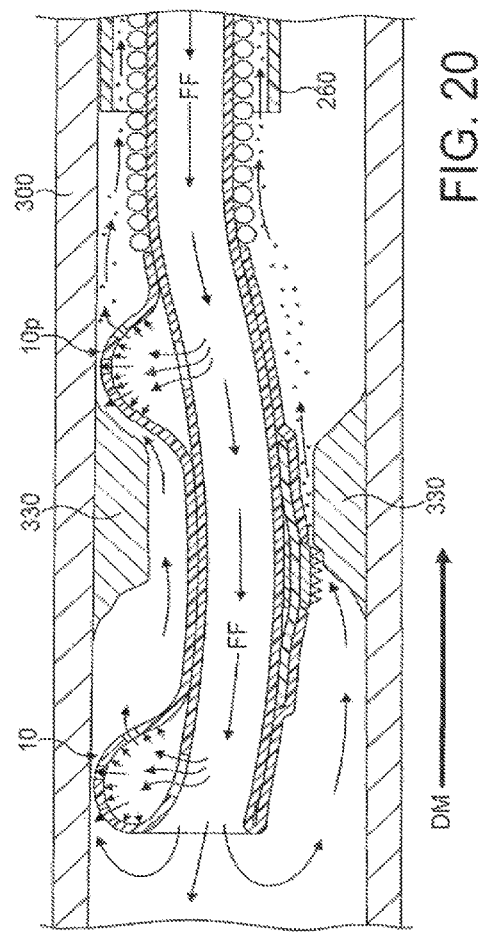
FIG. 19
FIG. 20

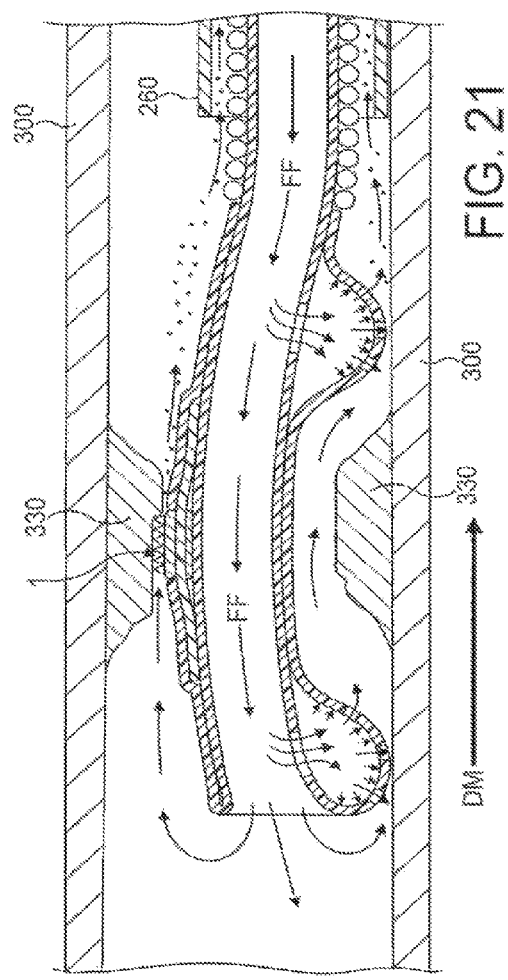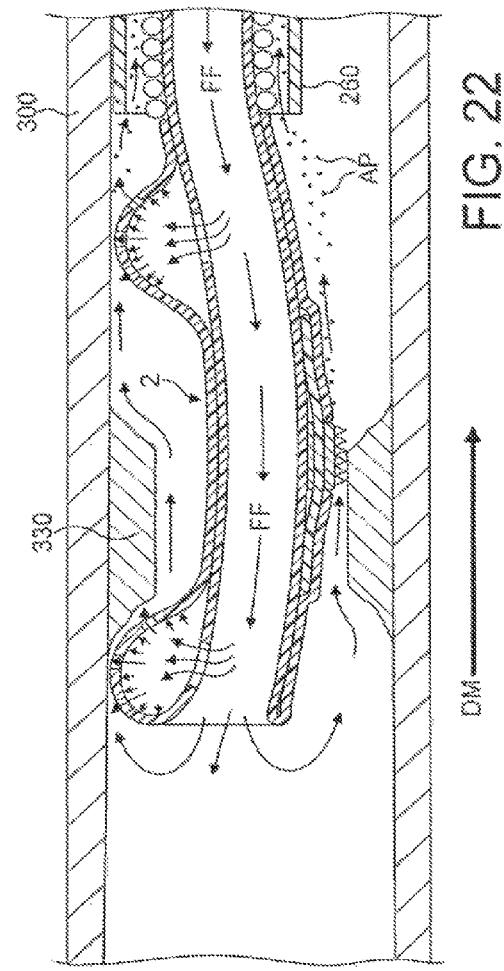

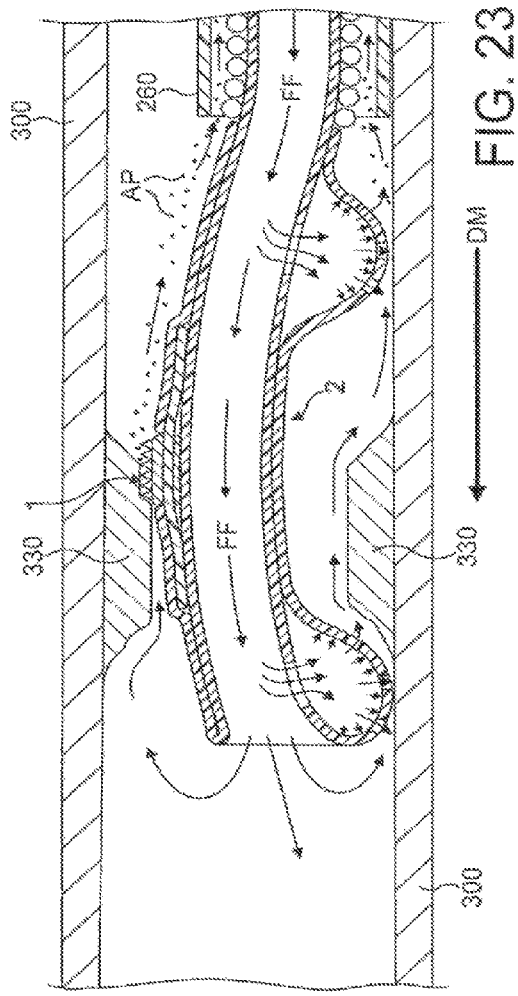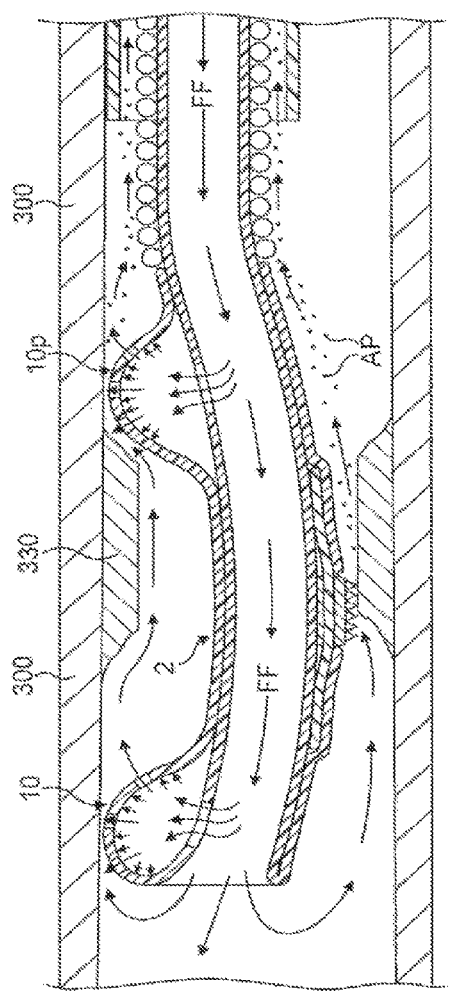

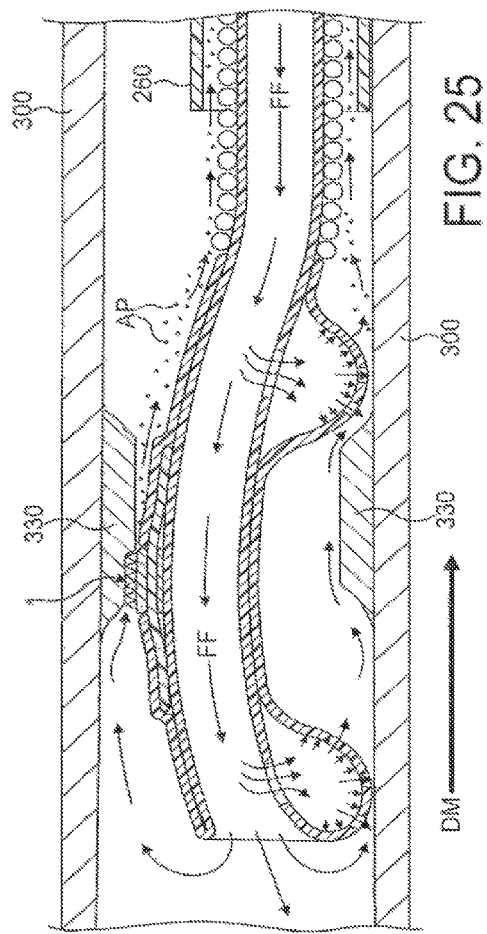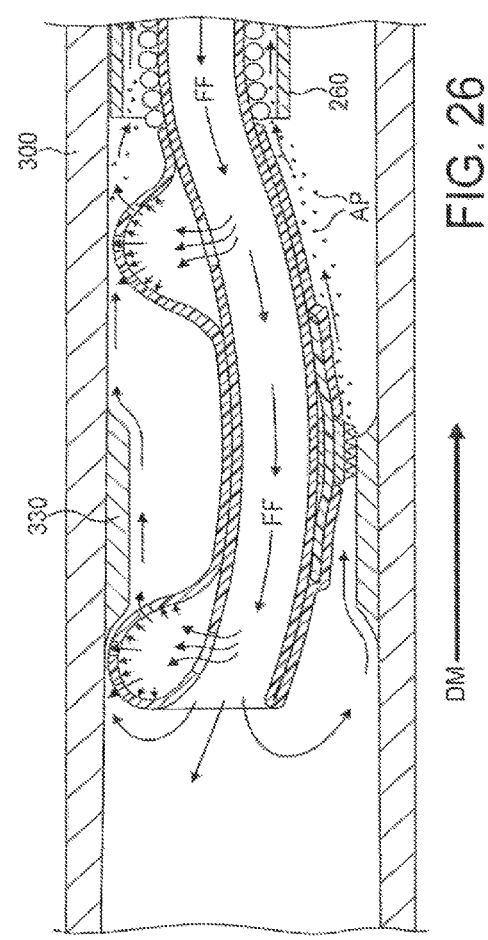

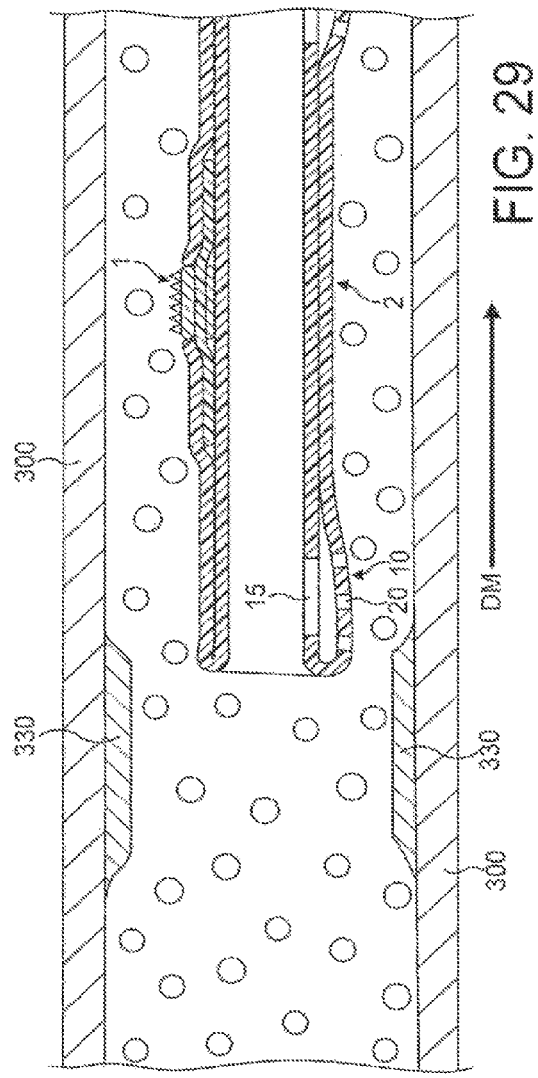
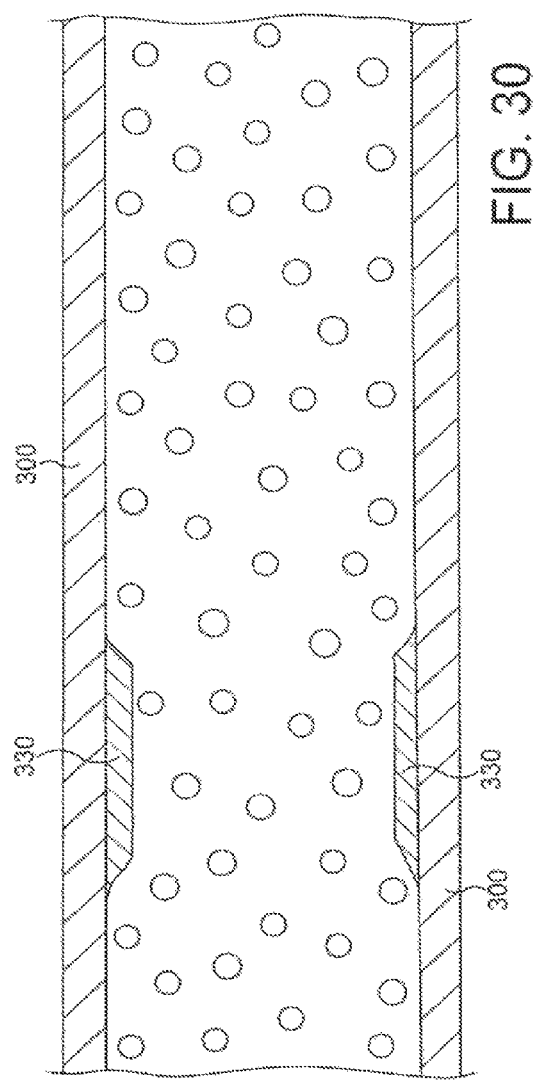

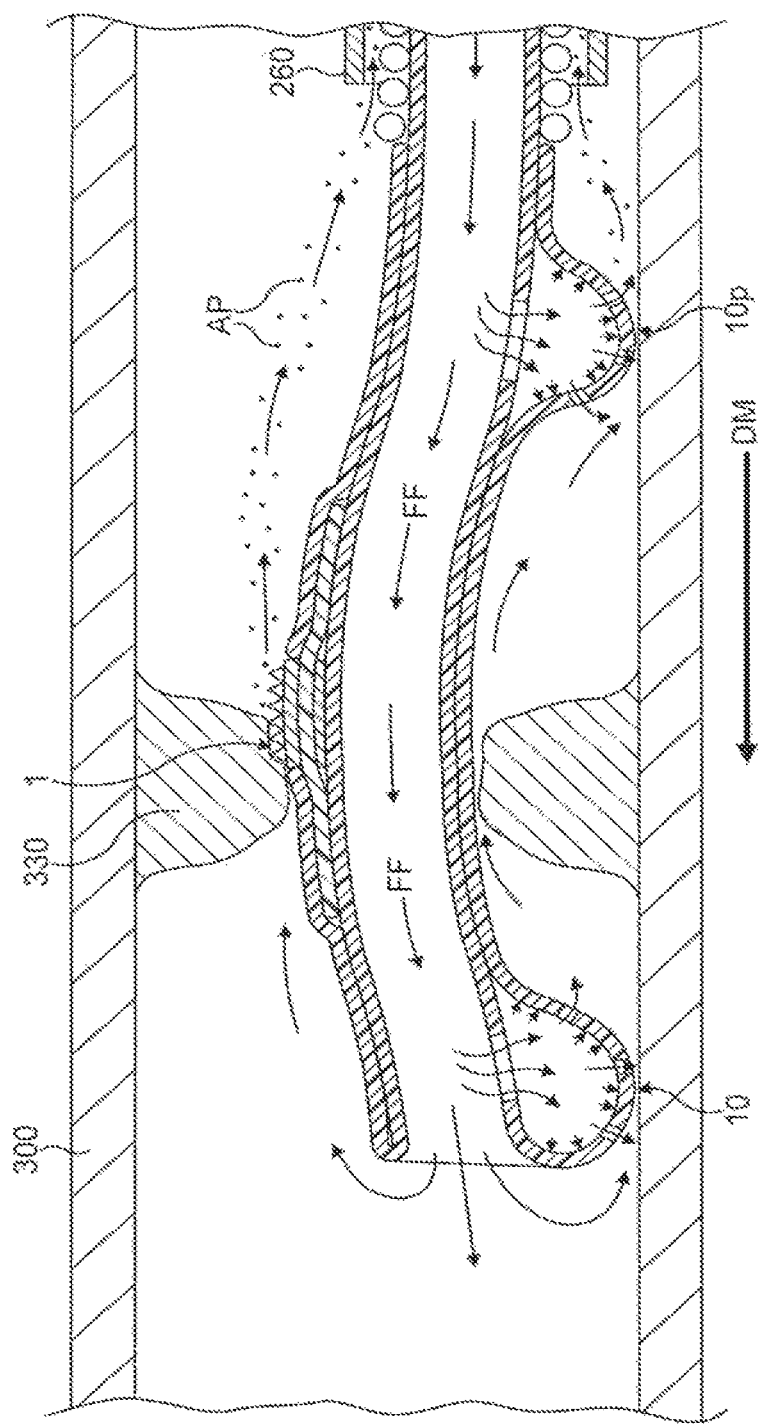

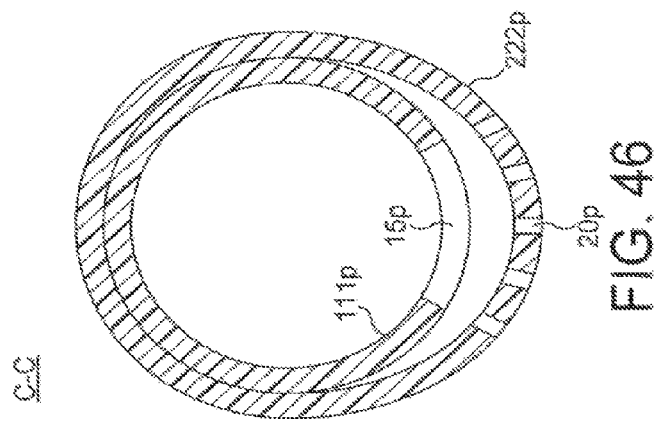
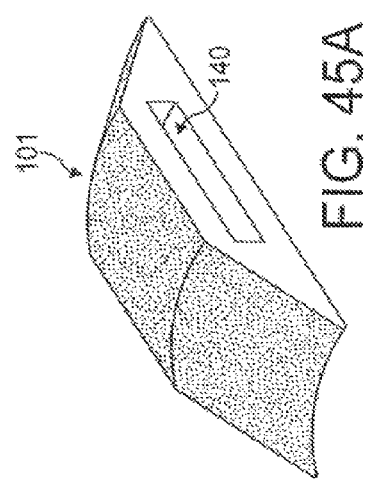
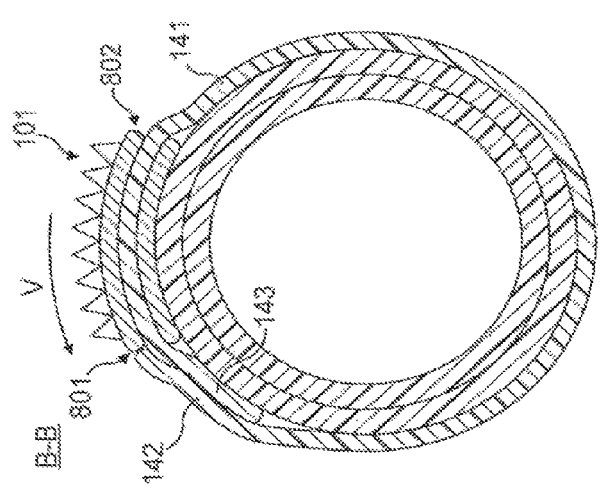
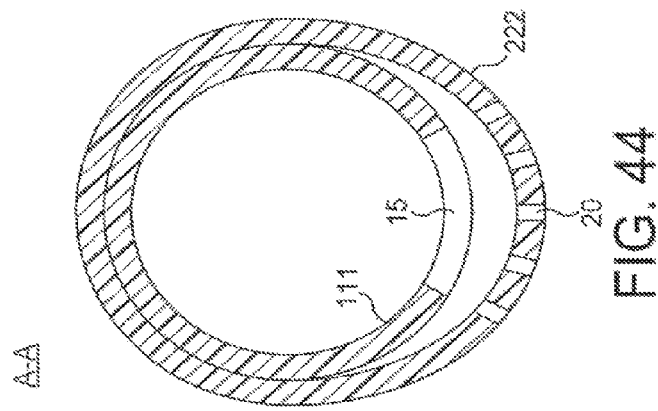

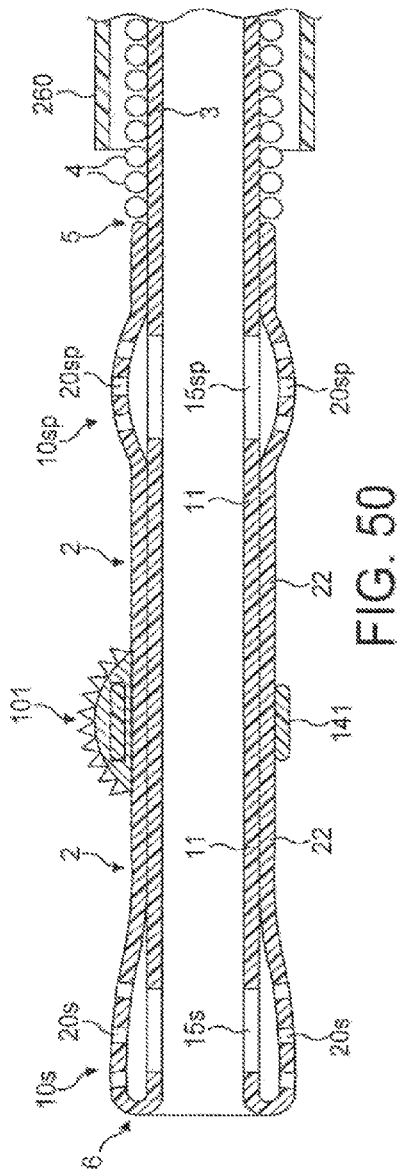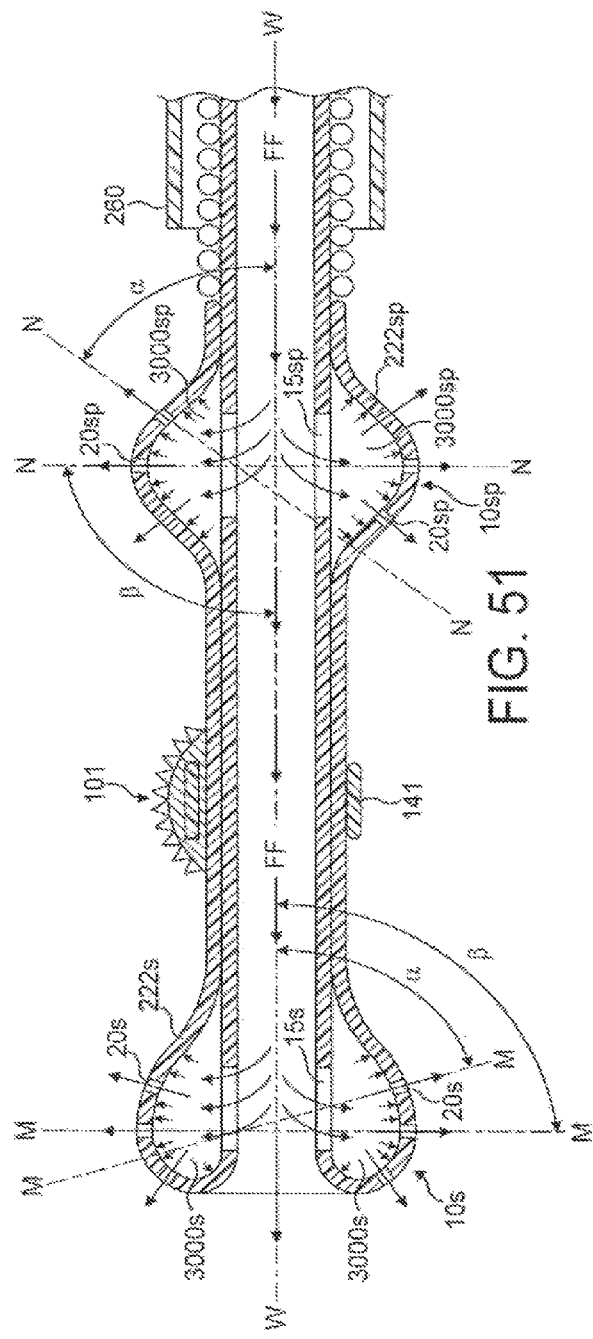

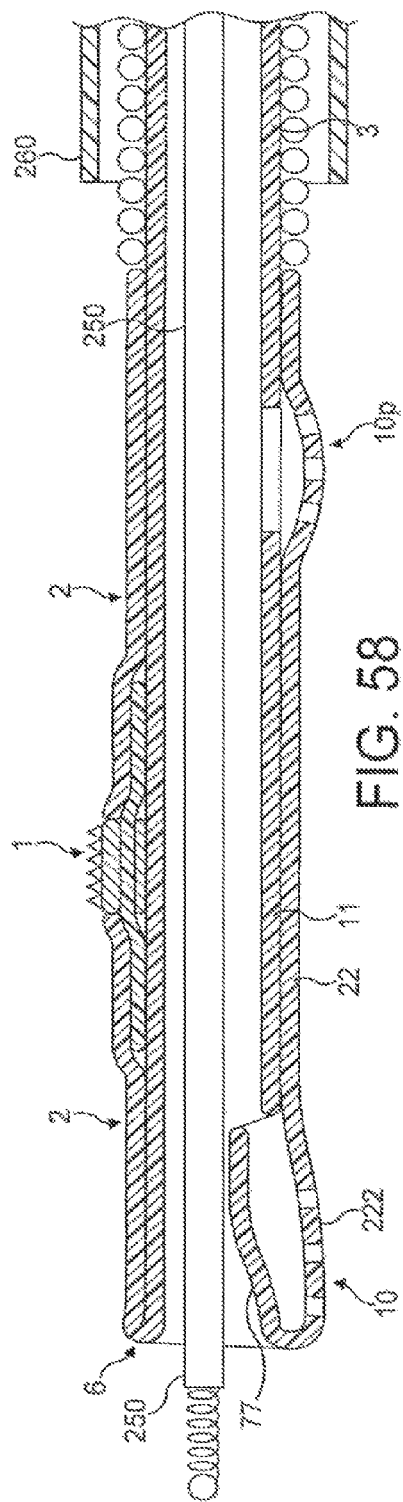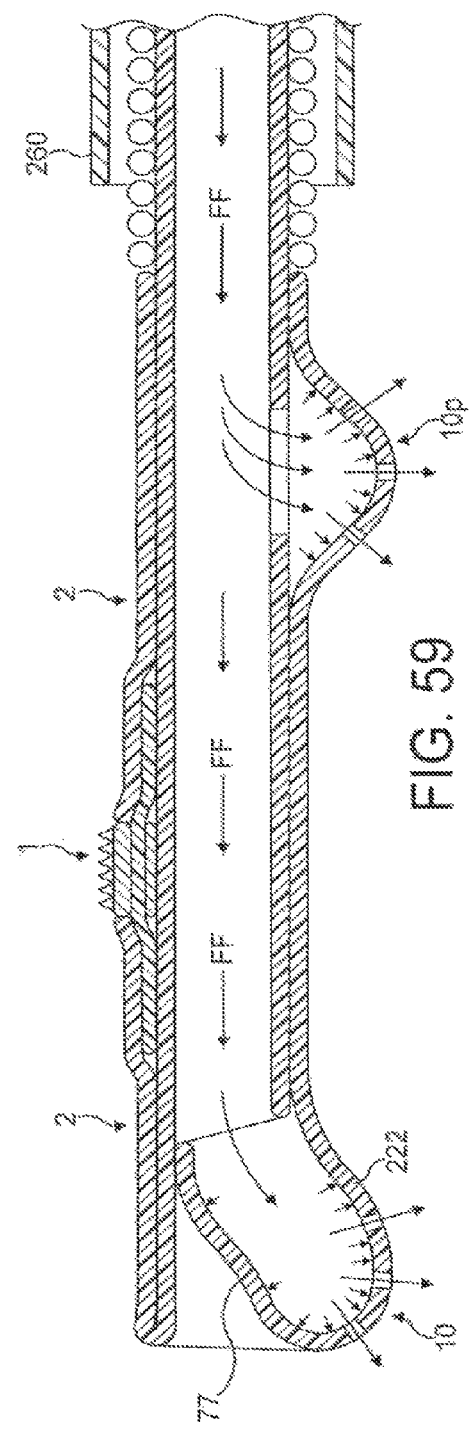

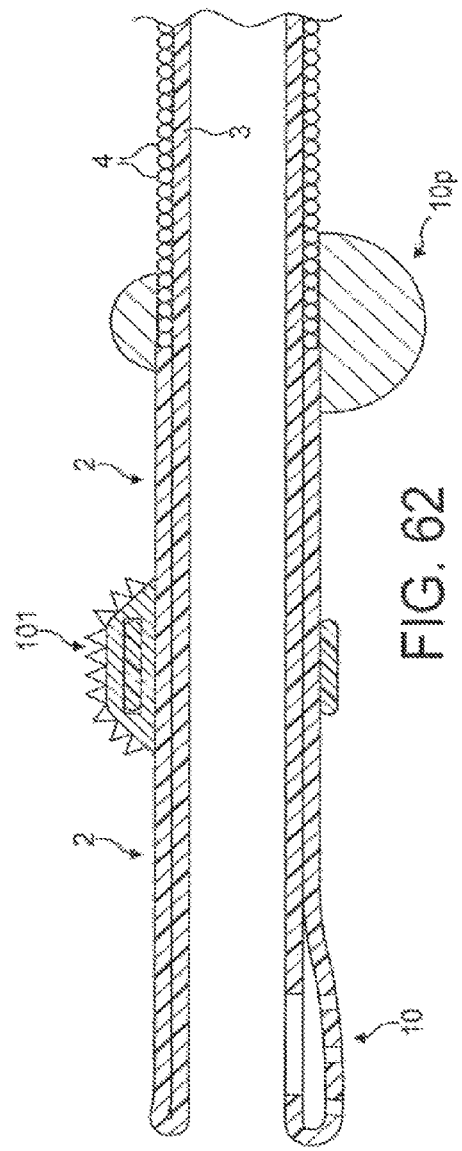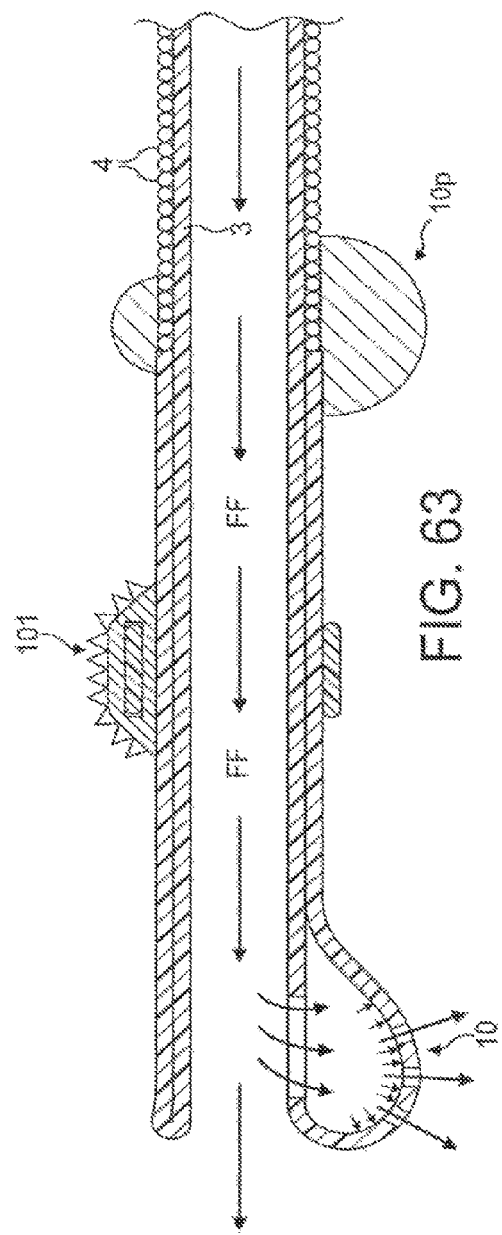

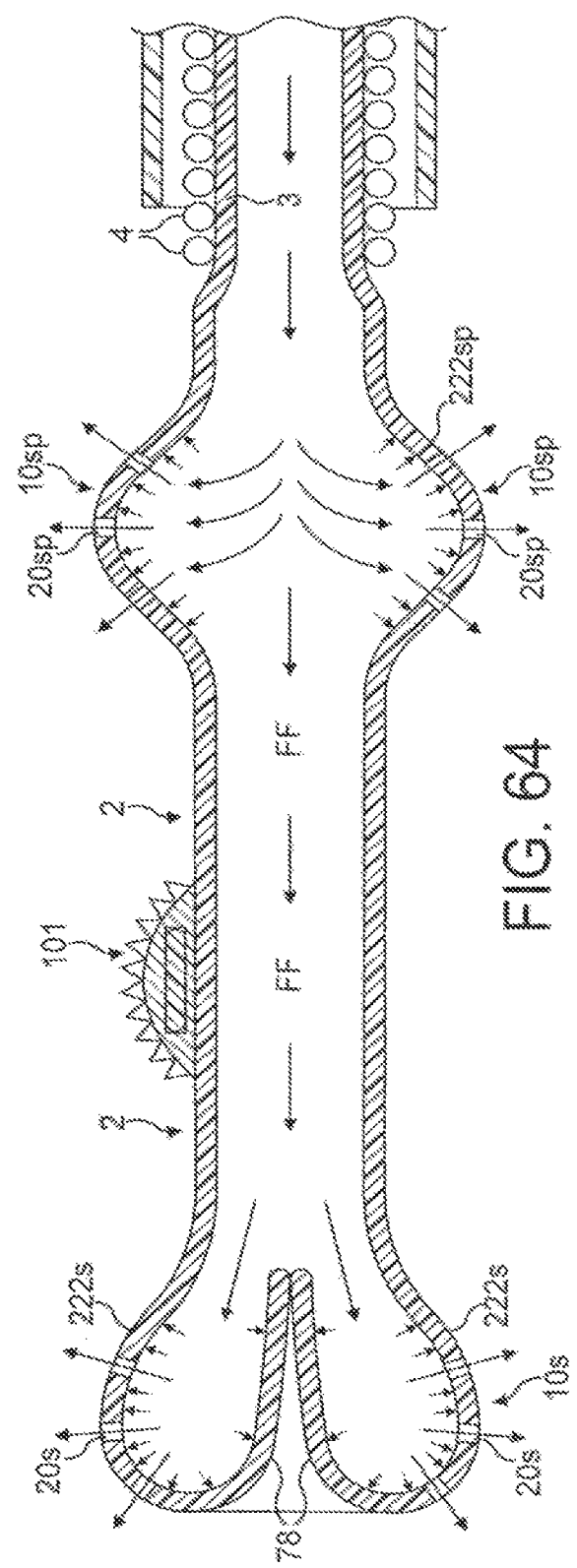

ROTATIONAL DEVICE WITH INFLATABLE SUPPORT ELEMENTS AND TORQUE TRANSMITTING MEMBRANE

CROSS-REFERENCE TO RELATED APPLICATIONS

This is a continuation of U.S. application Ser. No. 12/373,445 filed on Jan. 12, 2009 by Dr. Leonid Shturman, which is a national phase application based on PCT/EP2007/056516 filed on Jun. 28, 2007, which claims priority to GB Patent Application No. 0613981.0 filed on Jul. 13, 2006, the contents of these prior applications being incorporated herein by reference.

BACKGROUND

1. Field

The Present invention relates to a rotational atherectomy device for removing or reducing stenotic lesions in blood vessels such as a human artery by rotating an abrasive element within the vessel to partially or completely ablate the unwanted material.

2. Description of the Related Art

Atherosclerosis, the clogging of arteries, is a leading cause of coronary heart disease. Blood flow through the peripheral arteries (e.g., carotid, femoral, renal etc.), is similarly affected by the development of atherosclerotic blockages. A conventional method of removing or reducing blockages in blood vessels is known as rotational atherectomy. Such a method and a device for performing the method are described in, for example, U.S. Pat. No. 4,990,134 to Auth. According to Auth, a long guidewire is advanced into the diseased blood vessel across the stenotic lesion. A hollow drive shaft formed from a singe layer of torque transmitting coiled wire(s) is the advanced over the guidewire. The distal end of the drive shaft terminates in a burr provided with an abrasive surface formed from diamond grit or diamond particles. The burr is positioned against the occlusion and the drive shaft rotated at extremely high speeds (e.g., 20,000-160,000 rpm). As the burr rotates, the physician slowly advances it so that the abrasive surface of the burr scrapes against the occluding tissue and disintegrates it, reducing the occlusion and improving the blood flow through the vessel.

It is also known from U.S. Pat. No. 6,132,444 to Shturman (the instant inventor) et al., to provide a drive shaft with an eccentric enlarged diameter segment positioned proximally to and spaced away from the distal end of the drive shaft. According to U.S. Pat. No. 6,132,444 to Shturman, abrasive particles are located around a maximum diameter of said eccentric enlarged diameter segment of the drive shaft thereby forming an eccentric abrasive element positioned proximally to and spaced away from the distal end of the drive shaft. According to U.S. Pat. No. 6,132,444 to Shturman, the drive shaft is formed from a single layer of torque transmitting coiled wire(s).

The prior art rotational atherectomy devices such as those referred to above comprise an elongated drive shaft rotatable around a stationary guidewire. A long proximal portion of the drive shaft is rotatable within an elongated stationary drive shaft sheath, said drive shaft sheath forming an annular lumen between the stationary sheath and the rotatable drive shaft. A saline solution or special lubricating fluid is pumped into the annular lumen between the stationary sheath and the rotatable drive shaft. A portion of said saline solution or special lubricating fluid is able to pass between adjacent wire turns of the drive shaft into a second annular lumen formed between the drive shaft and the guidewire thereby reducing friction between the drive shaft and the guidewire. In all of the prior art rotational atherectomy devices referred to above the antegrade flowing saline solution or special lubricating fluid enters the treated vessel from distal end of the stationary drive shaft sheath and thereby entrains and propels distally in an antegrade direction along the treated vessel abraded particles (debris) removed by the abrasive element. The distal migration of the abraded particles (debris) in an antegrade direction and embolisation of very small diameter arteries or capillaries by said abraded particles is of major concern to physicians who practice in this field. Clearly, the existence of particulate matter in the blood stream is undesirable and can cause potentially life-threatening complications, especially if the particles are over a certain size.

Although the potentially detrimental effect caused by the presence of abraded particles in the blood vessels is reduced if they are very small microparticles, it is much more preferable to remove from the treated blood vessel any debris abraded or otherwise released from the stenotic lesion during treatment and thereby prevent migration of debris to other locations along the treated blood vessel.

A rotational atherectomy device, described in U.S. Pat. No. 5,681,336 (to Clement et al.), has been proposed. This device attempts to prevent migration of abraded particles distally along the treated blood vessel by removing the ablated material from the blood vessel whilst the device is in use. The rotational atherectomy device known from U.S. Pat. No. 5,681,336 (to Clement et al.) has a complicated construction and is difficult to manufacture on a commercial scale.

A number of disadvantages associated with the known rotational atherectomy devices have been addressed in WO 2006/126076 to Shturman (the instant inventor). All of the the embodiments described in WO 2006/126076 comprise a rotatable fluid impermeable drive shaft and allow delivery of pressurized fluid from a lumen of the rotatable fluid impermeable drive shaft into the treated vessel distal to the abrasive element so that at least a portion of said fluid flows in a retrograde direction along the treated vessel between the stenotic lesion and the vessel wall and entrains the abraded particles removed by the abrasive element. The retrograde flowing fluid and entrained abraded particles are aspirated from the treated vessel and out of the patient's body.

All embodiments shown in WO 2006/126076 illustrate a torque transmitting element of the fluid impermeable drive shaft being formed by a single multifilament metal torque transmitting coil which extends distally through and distal to the abrasive element. An atherectomy device having this design allows excellent transmission of torque to the abrasive element by the torque transmitting coil, but does not enable the device to have a sufficiently small transverse cross-sectional dimension to cross very tight stenotic lesions.

SUMMARY

The present invention seeks to provide a rotational atherectomy device with transverse cross-sectional dimensions sufficiently small to cross very tight stenotic lesions.

According to the present invention, there is provided a rotational atherectomy device for removing a stenotic tissue from a vessel of a patient, the device comprising a rotatable, flexible, hollow drive shaft having a fluid impermeable wall defining a fluid impermeable lumen of the drive shaft and, an abrasive element mounted to a distal end portion of the drive shaft proximal to and spaced away from a distal support element formed at a distal end of the drive shaft, the distal support element being inflatable by pressurized fluid which flows in an antegrade direction through said lumen of the drive shaft and is at least partially re-directed into the distal fluid inflatable support element, wherein the distal fluid inflatable support element has an outer wall comprising an outflow opening located such that said outflow opening faces an inner surface of a treated vessel during rotation of the drive shaft so that a flow of fluid through said outflow opening forms a layer of fluid between the outer wall of the rotating fluid inflated distal support element and a wall of the treated vessel to form a fluid bearing between the outer wall of the rotating fluid inflated distal support element and the wall of the treated vessel, wherein the shaft comprises at least one torque transmitting coil and at least one fluid impermeable membrane which extends beyond a distal end of the torque transmitting coil and conveys torque to the abrasive element mounted to the drive shaft distal to and spaced away from the distal end of the torque transmitting coil.

Preferably, the outer wall of the distal fluid inflatable support element has a plurality of outflow openings located such that at least one of said outflow openings, during rotation of the drive shaft, faces an inner surface of a treated vessel so that fluid flowing through the outflow openings forms a layer of fluid between the outer wall of the rotating fluid inflated distal support element and a wall of the treated vessel to form a fluid bearing between the outer wall of the rotating fluid inflated distal support element and the wall of the treated vessel.

In one embodiment of the invention, the abrasive element has a slot and is mounted to the drive shaft such that said slot extends in a longitudinal direction and is attached to the drive shaft by a flexible strap which extends through said slot and is connected to the drive shaft distal and proximal to the abrasive element.

In another embodiment, the abrasive element has a slot and is mounted to the drive shaft by a flexible strap which extends through said slot and is wrapped circumferentially around the drive shaft. Preferably, the abrasive element has a slot and is mounted to the drive shaft by a flexible strap which extends through said slot and is wrapped circumferentially around the drive shaft distal to and spaced away from the distal end of the torque transmitting coil.

The flexible strap may have leading and trailing edge portions relative to the direction of rotation of the drive shaft, wherein the trailing edge portion of the flexible strap at least partially overlaps the leading edge portion when wrapped around the drive shaft. The leading and trailing edge portions of the flexible strap can be bonded to each other in their overlapping region.

In one embodiment, the abrasive element has a leading edge and a trailing edge relative to the direction of rotation of the drive shaft, the leading edge of the abrasive element being thinner than the trailing edge so that, during rotation of the drive shaft, an abrasive surface of the abrasive element engages and abrades stenotic tissue only by a thicker portion of the abrasive element, said thicker portion of the abrasive element being spaced away from the leading edge of the abrasive element.

In another embodiment, the abrasive element has a rotationally leading edge and a rotationally trailing edge relative to the direction of rotation of the drive shaft, the rotationally leading edge of the abrasive element being thinner than the trailing edge so that the degree of engagement of the abrasive element with the stenotic tissue gradually increases during a revolution of the drive shaft. The abrasive element may extend around less than a half of the circumference of the drive shaft. Alternatively, the abrasive element extends around less than a third of a circumference of the drive shaft or, it may extend around the entire circumference of the drive shaft.

In one embodiment, the fluid impermeable drive shaft has a longitudinal axis and the distal fluid inflatable support element has a centre of mass offset from the longitudinal axis of the drive shaft when the distal inflatable support element is fluid inflated. Preferably, the outer wall of the distal fluid inflatable support element defines a fluid inflatable space that extends only partially around a circumference of the drive shaft so that, when the distal inflatable support element is fluid inflated, its centre of mass is offset from a longitudinal axis of the drive shaft in one direction, the distal fluid inflated support element acting, during rotation of the drive shaft, as a counterweight to the abrasive element which has its centre of mass offset from the longitudinal axis of the drive shaft in the opposite direction.

In one preferred embodiment, the fluid impermeable drive shaft is provided with a proximal fluid inflatable support element located proximal to and spaced away from the abrasive element, the proximal fluid inflatable support element having an outer wall. The proximal fluid inflatable support element may comprise an inner wall having an inflow aperture therein so that a portion of fluid flowing in an antegrade direction through the drive shaft is re-directed through the inflow aperture into the inflatable support element to inflate said proximal fluid inflatable support element.

In one embodiment, the proximal fluid inflatable support element has a centre of mass offset from the longitudinal axis of the drive shaft when the proximal inflatable support element is fluid inflated.

In one preferred embodiment, the outer wall of the proximal fluid inflatable support element comprises an outflow opening located such that said outflow opening faces an inner surface of a treated vessel during rotation of the drive shaft so that a flow of fluid through said outflow opening forms a layer of fluid between the outer wall of the rotating fluid inflated proximal support element and a wall of the treated vessel to form a fluid bearing between the outer wall of the rotating fluid inflated proximal support element and the wall of the treated vessel.

The outer wall of the proximal fluid inflatable support element preferably has a plurality of outflow openings located such that at least one of said outflow openings, during rotation of the drive shaft, faces an inner surface of a treated vessel so that fluid flowing through the outflow openings forms a layer of fluid between the outer wall of the rotating fluid inflated proximal support element and a wall of the treated vessel to form a fluid bearing between the outer wall of the rotating fluid inflated proximal support element and the wall of the treated vessel.

The outer wall of the proximal fluid inflatable support element preferably defines a fluid inflatable space that extends only partially around a circumference of the drive shaft so that, when the proximal inflatable support element is fluid inflated, its centre of mass is offset from a longitudinal axis of the drive shaft in one direction, the proximal fluid inflated support element acting, during rotation of the drive shaft, as a counterweight to the abrasive element which has its centre of mass offset from the longitudinal axis of the drive shaft in the opposite direction.

Preferably, in the first embodiment, the fluid inflatable space within both the distal and proximal fluid inflatable support elements extends circumferentially only partially around circumferential segments of the drive shaft which are spaced away in one direction with respect to the longitudinal axis of the drive shaft so that, when both the distal and proximal fluid inflatable support elements are inflated by fluid, their centers of mass become offset from a longitudinal axis of the drive shaft in said one direction and the distal and proximal fluid inflatable support elements act as counterweights to the abrasive element which is located on the drive shaft between the support elements and has its centre of mass offset from the longitudinal axis of the drive shaft in the opposite direction.

Conveniently, a fluid inflatable space within the distal fluid inflatable support element extends uniformly around an entire circumference of the drive shaft to provide the distal support element with a centre of mass which is coaxial with a longitudinal axis of the drive shaft when said distal support element is fluid inflated.

In one embodiment, there is a plurality of openings in the outer wall of the fluid inflatable distal support element, said openings being located around the circumference of the outer wall of the fluid inflatable distal support element such that, during rotation of the drive shaft, flows of fluid through the openings form a layer of fluid between the outer wall of the fluid inflated distal support element and a wall of the treated vessel, said layer of fluid forming a fluid bearing between the outer wall of the rotating fluid inflated distal support element and the wall of the treated vessel.

There may be a plurality of openings in the outer wall of the fluid inflatable distal support element, said openings being located around the circumference of the outer wall of the fluid inflatable distal support element such that, during rotation of the drive shaft, at least one of said openings faces an inner surface of a treated vessel, so that flows of fluid through the openings form a layer of fluid between the outer wall of the fluid inflated distal support element and a wall of the treated vessel, said layer of fluid forming a fluid bearing between the outer wall of the rotating fluid inflated distal support element and the wall of the treated vessel.

In one embodiment, a fluid inflatable space within the proximal fluid inflatable support element extends uniformly around an entire circumference of the drive shaft to provide a fluid inflated proximal support element with a centre of mass which is coaxial with a longitudinal axis of the drive shaft.

In one embodiment there is a plurality of openings in the outer wall of the fluid inflatable proximal support element, said openings being located around the circumference of the outer wall of the fluid inflatable proximal support element such that, during rotation of the drive shaft, flows of fluid through the openings form a layer of fluid between the outer wall of the fluid inflated proximal support element and a wall of the treated vessel, said layer of fluid forming a fluid bearing between the outer wall of the rotating fluid inflated proximal support element and the wall of the treated vessel. Preferably, there is a plurality of openings in the outer wall of the fluid inflatable proximal support element, said openings being located around the circumference of the outer wall of the fluid inflatable proximal support element such that, during rotation of the drive shaft, at least one of said openings is facing an inner surface of a treated vessel so that flows of fluid through the openings form a layer of fluid between the outer wall of the fluid inflated proximal support element and a wall of the treated vessel, said layer of fluid forming a fluid bearing between the outer wall of the rotating fluid inflated proximal support element and the wall of the treated vessel.

In one embodiment, the fluid impermeable membrane extends distally under and beyond the abrasive element and is folded on itself at a distal end of the drive shaft to form the distal fluid inflatable support element between an inner and outer layers of said folded membrane, the outer layer of the membrane forming an outer wall of the distal fluid inflatable support element and the inner layer of the membrane forming an inner wall of the distal fluid inflatable support element, the inner wall of the inflatable support element having an aperture therein so that a portion of fluid flowing in an antegrade direction through the drive shaft is re-directed through the aperture into the distal fluid inflatable support element to inflate said distal support element.

The inner and outer layers of the folded fluid impermeable membrane may be connected or bonded to each other at least just proximal to the distal fluid inflatable support element. Preferably, the inner and outer layers of the folded fluid impermeable membrane should be connected or bonded to each other around an entire circumference of the drive shaft.

In one embodiment, the outer layer of the folded fluid impermeable membrane, after forming the outer wall of the distal fluid inflatable support element, extends further proximally to form an outer wall of the proximal fluid inflatable support element. The inner and outer layers of the folded fluid impermeable membrane should be connected or bonded to each other at least just distal and proximal to the proximal fluid inflatable support element.

The distal fluid inflatable support element preferably has an inner wall defined by the inner layer of the fluid impermeable membrane, the inner wall having an aperture therein so that a portion of the fluid flowing in an antegrade direction through the drive shaft is redirected through the aperture into the proximal fluid inflatable support element to inflate said proximal support element. Preferably, the aperture through which fluid enters the distal inflatable support element and the opening(s) in the outer wall of the inflated distal inflatable support element through which fluid exits the distal inflatable support element are configured so that the distal inflatable support element is kept inflated by the pressure of the fluid flowing through the inflatable support element.

The aperture through which fluid enters the distal inflatable support element should be larger than the opening(s) in the outer wall of the inflated distal inflatable support element through which fluid exits the distal inflatable support element so that the distal inflatable support element is kept inflated by the pressure of the fluid flowing through the inflatable support element.

In one embodiment, the abrasive element has a slot and is mounted to the drive shaft by a flexible strap which extends through said slot and is wrapped around the membrane proximal to and spaced away from the distal fluid inflatable support element. The flexible strap is, preferably, wrapped around the membrane distal to and spaced away from the distal end of the torque transmitting coil. Preferably, the flexible strap is wrapped around the outer layer of the folded fluid impermeable membrane.

In another embodiment, the abrasive element has a slot and is mounted to the drive shaft such that said slot extends in a longitudinal direction and is attached to the fluid impermeable membrane by a flexible strap which extends through said slot and is connected to the drive shaft distal and proximal to the abrasive element. The outer layer of the folded fluid impermeable membrane, after forming the outer wall of the distal fluid inflatable support element, may extend further proximally to form an outer wall of the proximal fluid inflatable support element, wherein the flexible strap, which mounts the abrasive element to the drive shaft, extends between the inner and outer layers of the folded fluid impermeable membrane both distal and proximal to the abrasive element.

The outer layer of the folded fluid impermeable membrane conveniently has an opening through which an abrasive surface of the abrasive element at least partially protrudes above a surface of the outer layer of the folded fluid impermeable membrane.

In another embodiment, a flexible leaf valve is formed near the distal end of the drive shaft. The flexible leaf valve may be formed integrally with the outer wall of the distal fluid inflatable support element, said flexible valve having a distal end which is continuous with the outer wall of the fluid impermeable membrane and a proximal edge which is free and is movable across a lumen of the drive shaft.

Preferably, the flexible valve is moved to its open position by a guidewire when the drive shaft is advanced over a guidewire, the guidewire moving the flexible valve radially outward.

The flexible valve can be moved to its closed position by pressure of fluid, which is pumped in an antegrade direction through the fluid impermeable drive shaft after advancing the drive shaft over a guidewire across a stenotic lesion to be treated and after withdrawing the guidewire from the drive shaft.

In another embodiment, the wall of the fluid impermeable drive shaft is comprised of two torque transmitting coils and at least one fluid impermeable membrane which extends beyond distal ends of the torque transmitting coils and conveys torque to the abrasive element mounted to the drive shaft distal to and spaced away from the distal ends of the torque transmitting coils. The torque transmitting coils can be disposed coaxially with respect to each other, one of two coils being an inner torque transmitting coil and the other torque transmitting coil being an outer torque transmitting coil, the inner and the outer torque transmitting coils being wound in opposite directions so that, when the drive shaft is rotated, the outer torque transmitting coil prevents unwinding of the inner torque transmitting coil.

In one embodiment, the fluid impermeable membrane lines the torque transmitting coil. The fluid impermeable membrane may line the inner torque transmitting coil. Alternatively, the fluid impermeable membrane is disposed around the torque transmitting coil. Preferably, the fluid impermeable membrane is disposed around the outer torque transmitting coil.

According to another embodiment of the invention, there is provided a rotational atherectomy device for removing a stenotic tissue from a vessel of a patient, the device comprising an abrasive element mounted to a rotatable, flexible, hollow drive shaft, the drive shaft comprised by a fluid impermeable membrane and a torque transmitting coil, the torque transmitting coil being lined by the fluid impermeable membrane which extends beyond a distal end of the coil to convey torque to the abrasive element attached to the membrane distal to and spaced away from the distal end of the coil, the fluid impermeable membrane extending distally beyond the abrasive element and being folded back on itself at a distal end of the drive shaft to form a distal fluid inflatable support element between an inner and outer layers of said folded membrane, the outer layer of the membrane forming an outer wall of the distal fluid inflatable support element and the inner layer of the membrane forming an inner wall of the distal fluid inflatable support element, the inner wall of the inflatable support element having an aperture therein so that a portion of fluid flowing in an antegrade direction through the drive shaft is re-directed through the aperture into the inflatable support element to inflate said distal fluid inflatable support element.

According to another embodiment of the invention, there is provided a rotational atherectomy device for removing a stenotic lesion from within a vessel of a patient, the device comprising a rotatable, flexible, hollow drive shaft having a longitudinal axis of rotation and an abrasive element mounted on a region of the drive shaft proximal to and spaced away from a distal fluid inflatable support element formed at a distal end of the drive shaft by a fluid impermeable membrane which defines at least an outer wall of the distal fluid inflatable support element, the distal fluid inflatable support element including at least two openings, an inflow opening communicating a fluid impermeable lumen of the drive shaft with an inflatable space of the distal fluid inflatable support element and an outflow opening located in the outer wall of the distal fluid inflatable support element, said outflow opening having an axis which forms an acute angle of over 60 degrees with the longitudinal axis of the drive shaft when the distal fluid inflatable element is inflated.

According to yet another embodiment of the invention, there is provided a rotational atherectomy device for removing a stenotic lesion from within a vessel of a patient, the device comprising a rotatable, flexible, hollow drive shaft having a longitudinal axis of rotation and an abrasive element mounted on a region of the drive shaft proximal to and spaced away from a distal fluid inflatable support element formed at a distal end of the drive shaft by a fluid impermeable membrane which defines at least an outer wall of the distal fluid inflatable support element, the distal fluid inflatable support element including at least two openings, an inflow opening communicating a fluid impermeable lumen of the drive shaft with an inflatable space of the distal fluid inflatable support element and an outflow opening located in the outer wall of the distal fluid inflatable support element and communicating the interior space of the distal fluid inflatable support element with a vascular space within the vessel of the patient, said outflow opening having an axis which forms an angle of about ninety (90) degrees with the longitudinal axis of the drive shaft when the distal fluid inflatable element is inflated.

According to yet another embodiment of the invention, there is provided a rotational atherectomy device for removing a stenotic lesion from within a vessel of a patient, the device comprising a rotatable, flexible, hollow drive shaft having a longitudinal axis of rotation and an abrasive element mounted proximal to and spaced away from its distal end, the drive shaft including two fluid inflatable support elements, a distal fluid inflatable support element located at the distal end of the drive shaft and spaced away from the abrasive element and, a proximal fluid inflatable support element located proximal to and spaced away from the abrasive element, each of the fluid inflatable elements includes at least one inflow opening which communicates a fluid impermeable lumen of the drive shaft with inflatable spaces of the fluid inflatable support elements, each said inflatable space being defined by a fluid impermeable membrane which forms at least outer walls of the distal and proximal fluid inflatable support elements, the outer walls of both the distal and proximal fluid inflatable support elements comprising outflow openings located such that at least one of the outflow openings of each fluid inflatable support element having an axis which forms an angle of about ninety (90) degrees with the longitudinal axis of the drive shaft when the fluid inflatable elements are inflated.

According to yet another embodiment of the invention, there is provided a rotational atherectomy device, wherein the drive shaft is provided with a solid proximal support element located proximal to and spaced away from the abrasive element, the membrane that forms a fluid impermeable lumen for the antegrade flow of fluid through the drive shaft into the distal fluid inflatable support element also forming a lumen for the antegrade flow of fluid through the drive shaft into an outflow channel extending through said solid proximal support element, the solid proximal support element having a rounded outer surface, said outflow channel having an outflow opening in the rounded outer surface of the solid proximal support element such that, during rotation of the drive shaft, said outflow opening on the outer surface of the solid proximal support element is facing an inner surface of a treated vessel so that a flow of fluid out of said outflow opening forms a layer of fluid between the solid proximal support element and a wall of the treated vessel during rotation of the drive shaft, said layer of fluid forming a fluid bearing between the rotating solid proximal support element and the wall of the treated vessel.

It should be appreciated that the present invention covers two most preferred embodiments namely, a first most preferred embodiment in which the fluid inflatable support elements are asymmetrical with respect to the longitudinal axis of the drive shaft and, a second most preferred embodiment in which the fluid inflatable support elements are symmetric with respect to the longitudinal axis of the drive shaft. However, it will be appreciated that, in all the embodiments, the asymmetric and symmetric fluid inflatable elements comprise outflow openings located such that, in the rotating drive shaft, fluid flowing through said openings forms fluid bearings between outer walls of said inflatable elements and the wall of the treated vessel.

It should be noted that throughout this specification, reference is made to "distal" and "proximal" ends and to flow of fluid in an "antegrade" and "retrograde" direction. For the avoidance of doubt, the distal end is considered to refer to the end of the device which is inserted into the vessel in the body of the patient and the proximal end is the end of the device which remains outside the body of the patient and which can be connected to a handle assembly for both rotating and longitudinally moving the drive shaft within the treated vessel. "Antegrade" flow refers to a direction of flow from the proximal towards the distal end of the device. Similarly, "retrograde" flow refers to a direction of flow in the opposite direction, i.e. from the distal towards the proximal end of the device.

BRIEF DESCRIPTION OF THE DRAWINGS

Embodiments of the invention will now be described, by way of example only, in conjunction with the following drawings, in which:

FIG. 1 is a side sectional view of the distal end portion of the rotational atherectomy device illustrating attachment of an abrasive element to a fluid impermeable drive shaft by a longitudinally extending strap and showing fluid inflatable support elements of the drive shaft in their deflated state;

FIG. 2 is similar to FIG. 1, except it illustrates flow of fluid into and out of the inflated support elements, the fluid inflated support elements having their centers of mass spaced radially away from the longitudinal axis of the drive shaft;

FIG. 9 is a sectional side elevation of a portion of a blood vessel containing a stenotic lesion and shows a guidewire which has been already advanced across the stenotic lesion to be treated;

FIG. 10 is a side sectional view of the portion of the blood vessel shown in FIG. 9 and illustrates advancement of the fluid impermeable drive shaft over the guidewire;

FIG. 11 is similar to FIG. 10, but illustrates that the drive shaft has been advanced over the guidewire across the stenotic lesion to a position in which a distal fluid inflatable support element is located distal to the stenotic lesion and a proximal fluid inflatable support element is still proximal to the stenotic lesion to be treated;

FIG. 12 is a side sectional view illustrating withdrawal of the guidewire from the drive shaft;

FIG. 13 is a side sectional view illustrating that the guidewire has been completely withdrawn from the drive shaft;

FIG. 14 is a side sectional view illustrating antegrade flow of fluid along the fluid impermeable drive shaft, inflation of the fluid inflatable support elements and retrograde flow of fluid around the drive shaft;

FIGS. 15 through 26 illustrate abrading of the stenotic lesion by the rotating abrasive element and formation of fluid bearings between the inner surface of the vessel and the outer walls of the rotating fluid inflated support elements, said fluid bearings being formed by flow of fluid through the openings in the outer walls of the fluid inflated support elements;

FIGS. 29 and 30 illustrate the removal of the drive shaft from the treated vessel and appearance of the treated vessel after removal of the drive shaft;

FIGS. 31 through 34 are similar to FIGS. 15 through 26 except that they illustrate abrading of a very tight stenotic lesion from a large diameter vessel by the rotational atherectomy device with a small diameter drive shaft;

FIGS. 42 through 49 are similar to FIGS. 1 through 8 except that they illustrate that the abrasive element is attached to the drive shaft by a flexible strap which extends around the drive shaft;

FIG. 50 is similar to FIG. 42 except that it illustrates fluid inflatable support elements which extend around the entire circumference of the drive shaft;

FIG. 51 is similar to FIG. 43 except that it illustrates flow of fluid into and out of the fluid inflated support elements which extend around the entire circumference of the drive shaft;

FIG. 58 illustrates the rotational atherectomy device with a flexible leaf valve located at the distal end of a fluid impermeable drive shaft, said leaf valve being moved to its open position by a guidewire around which the drive shaft is advanced across the stenotic lesion to be treated;

FIG. 59 shows that the flexible leaf valve located at the distal end of the drive shaft is moved to its closed position by pressure of flushing fluid after the guidewire has been withdrawn from the drive shaft, the flexible leaf valve shown in FIGS. 58 and 59 having one or more leaflets;

FIG. 62 illustrates the distal end portion of the drive shaft with an asymmetric fluid inflatable distal support element and a solid asymmetric proximal support element, the fluid inflatable support element shown in its deflated state;

FIG. 63 illustrates the distal end portion of the drive shaft with an asymmetric fluid inflatable distal support element and a solid asymmetric proximal support element, the fluid inflatable support element shown in its inflated state and;

FIG. 64 shows a rotational atherectomy device with symmetric fluid inflatable support elements which are formed integrally with a fluid impermeable membrane without folding the membrane on itself at the distal end of the drive shaft but instead making said inflatable support elements integral with the membrane by using manufacturing methods of injection molding, insertion molding or other currently available progressive manufacturing methods.

DETAILED DESCRIPTION

Figure 3:
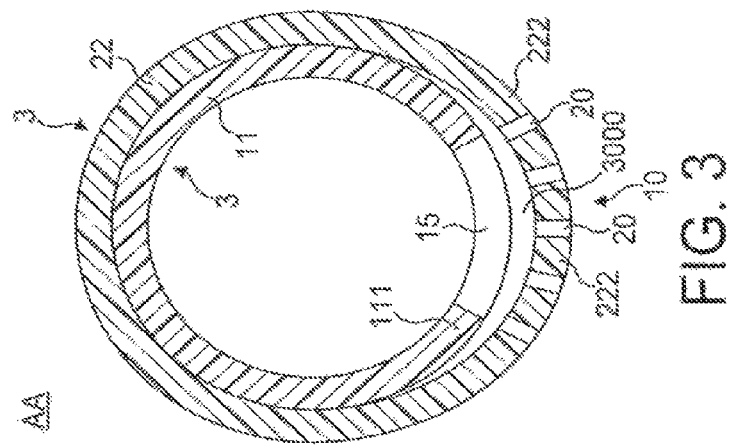
FIG. 3 shows an enlarged cross-sectional view of the distal fluid inflatable support element taken along a line A-A in FIG. 1.

In FIGS. 1 to 64, the atherectomy device is advanced across the stenotic lesion 330 over the guidewire 250. The direction of movement of the device is indicated by arrow marked "DM", the antegrade flow of fluid being indicated by arrows "FF" and the flow of fluid in a retrograde direction is indicated by arrows marked "R". Arrows marked "FP" designate pressure of fluid which distends the support elements. Abraded particles AP abraded from the stenotic lesion 330 are aspirated into a lumen of a drive shaft sheath 260 so that the retrograde flowing fluid and the abraded particles entrained in said fluid can be removed from the treated vessel and out of the patient's body.

FIGS. 1 through 8 illustrate in longitudinal and transverse cross-sections a distal portion of the first most preferred embodiment of the rotational atherectomy device of the invention. The rotational atherectomy device is comprised of an abrasive element 1 which is mounted to a rotatable, flexible, hollow, fluid impermeable drive shaft 2. The fluid impermeable drive shaft 2 is comprised by a fluid impermeable membrane 3 and a torque transmitting coil 4. The torque transmitting coil 4 is lined by the fluid impermeable membrane 3 which extends distally beyond the distal end 5 of the coil 4. The fluid impermeable membrane 3 alone conveys torque further distally from the distal end 5 of the coil 4 to the abrasive element 1 which is attached to the membrane 3 distal to and spaced away from the distal end 5 of the coil 4. The fluid impermeable membrane 3 extends distally beyond the abrasive element 1 and is folded on itself at a distal end 6 of the drive shaft 2 to form a distal fluid inflatable support element 10 between an inner 11 and outer 22 layers of the folded membrane 3. The outer layer 22 of the membrane 3 forms an outer wall 222 of the distal fluid inflatable support element 10 and the inner layer 11 of the membrane 3 forms an inner wall 111 of the distal fluid inflatable support element 10. The inner wall 111 of the distal fluid inflatable support element 10 has an inflow aperture 15 therein.

FIG. 2 shows that the inflow aperture (opening) 15 of the distal fluid inflatable support element 10 communicates a lumen of the fluid impermeable drive shaft 2 with a fluid inflatable space 3000 of the distal fluid inflatable support element 10. The Figure illustrates that a portion of flushing fluid FF flowing in an antegrade direction through the drive shaft 2 is redirected through the inflow aperture 15 into the distal fluid inflatable support element 10 to inflate said support element 10.

It should be noted that the inner 11 and the outer 22 layers of the folded membrane may be formed by either folding the membrane 3 back onto itself or by inverting it.

FIG. 2 best illustrates that in order to form the distal fluid inflatable support element 10, the inner 11 and outer 22 layers of the folded fluid impermeable membrane 3 are connected or bonded to each other at least just proximal to the distal fluid inflatable support element 10. In this location, just proximal to the distal fluid inflatable support element 10, the inner 11 and the outer 22 layers of the membrane 3 are preferably connected or bonded directly to each other around the entire circumference of the drive shaft 2.

Figure 6:
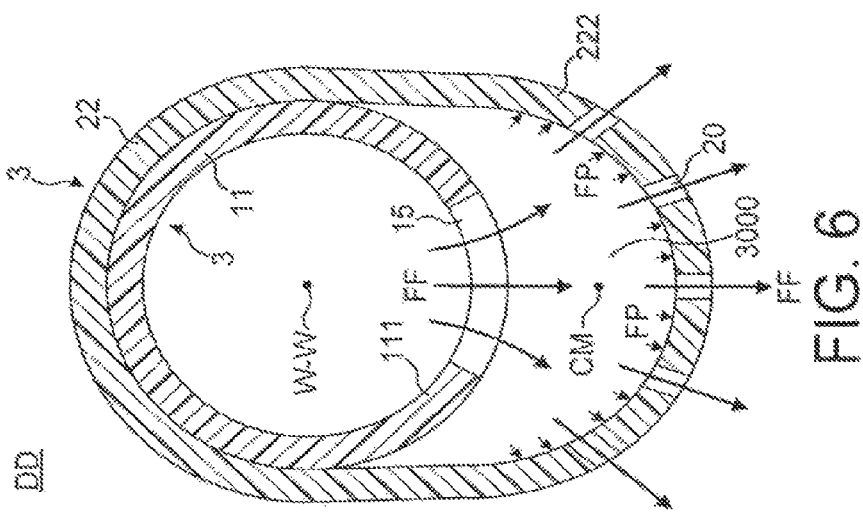
FIG. 6 shows an enlarged cross-sectional view taken along a line D-D in FIG. 2 and illustrates flow of fluid into and out of the distal fluid inflated support element.
Figure 27:
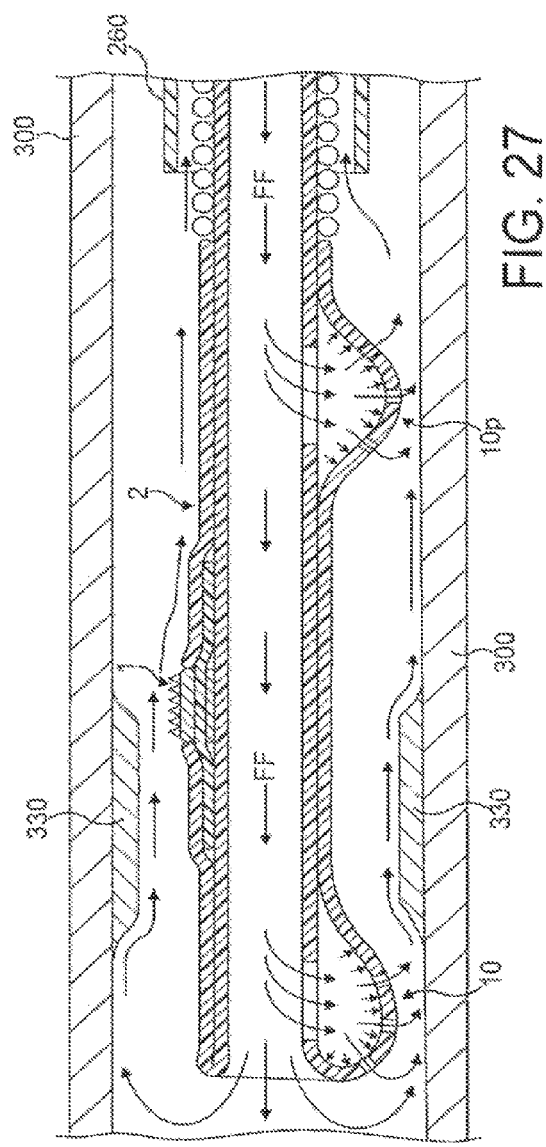
FIG. 27 illustrates that antegrade flow of fluid through the drive shaft and retrograde flow of fluid across the treated stenotic lesion is continued for at least a short period of time after rotation of the drive shaft has been stopped.
Figure 28:
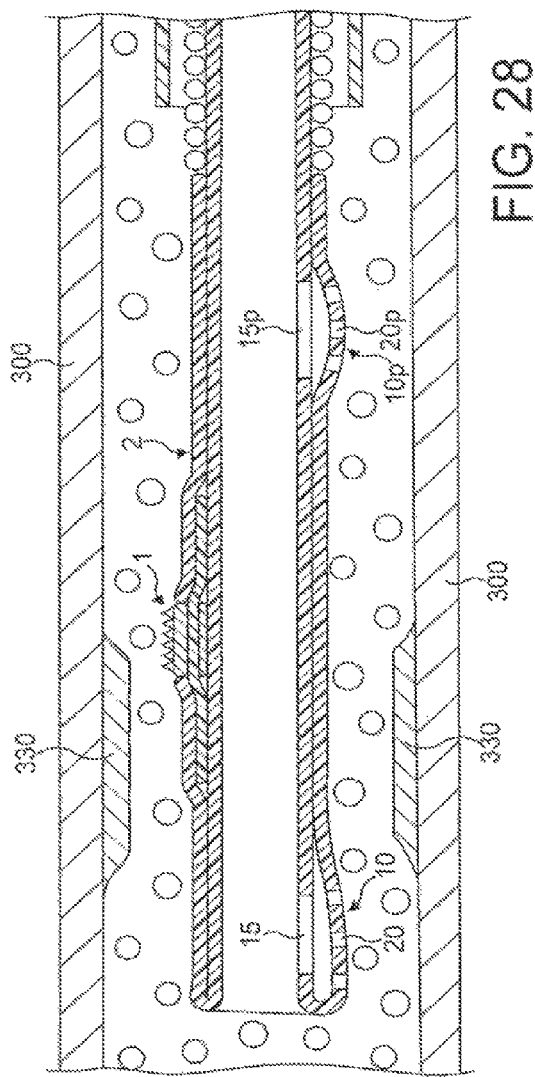
FIG. 28 illustrates that the fluid inflatable support elements have been deflated and the drive shaft is ready to be removed from the treated vessel.
Figure 32:
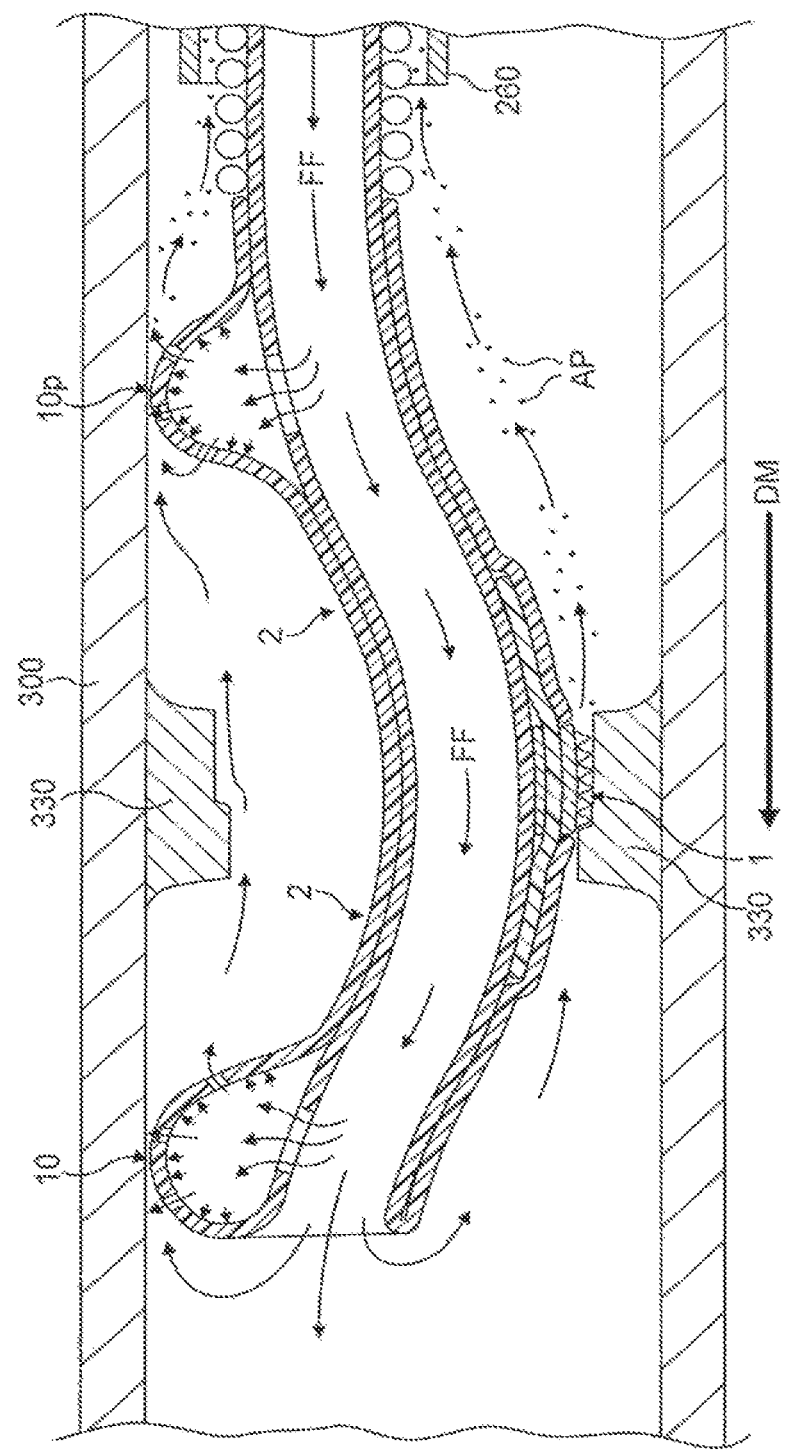
Figure 33:
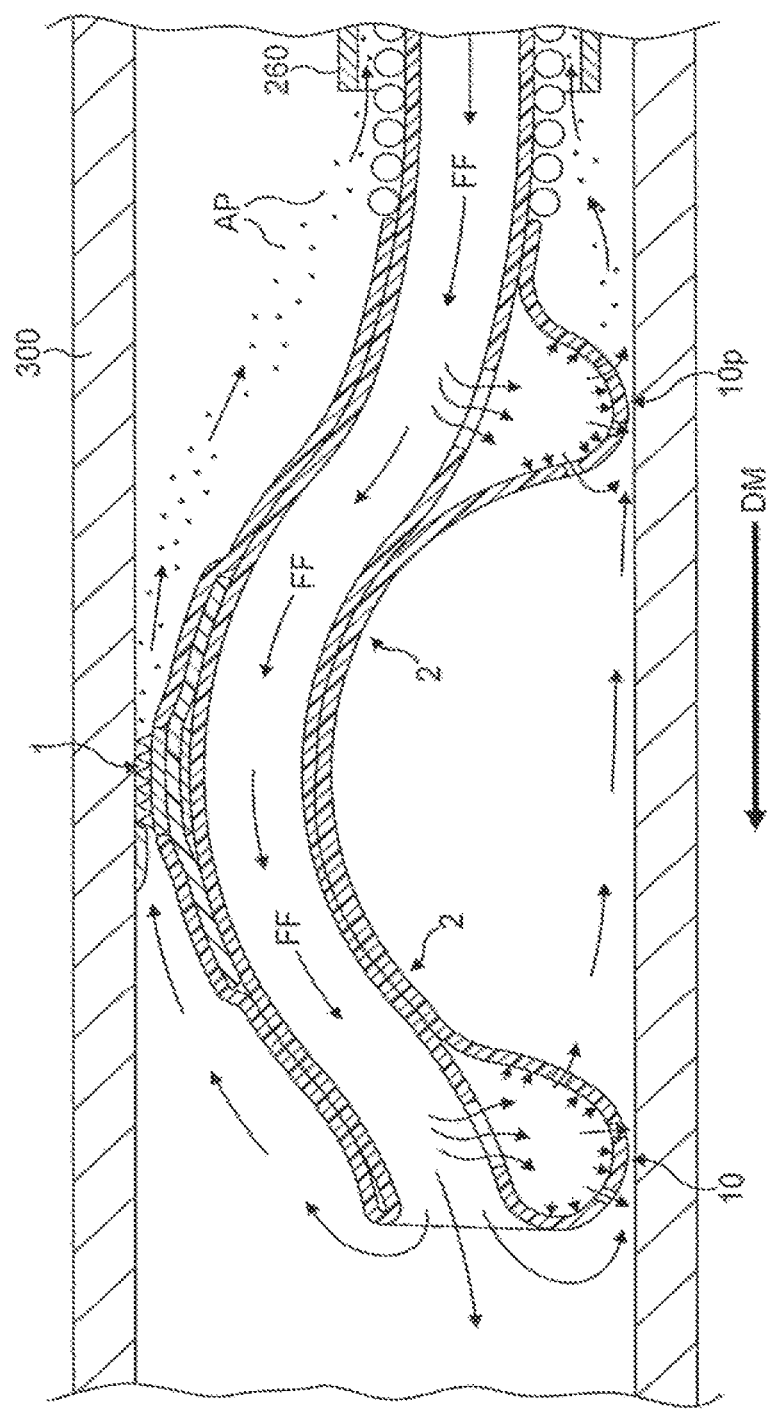
Figure 34:
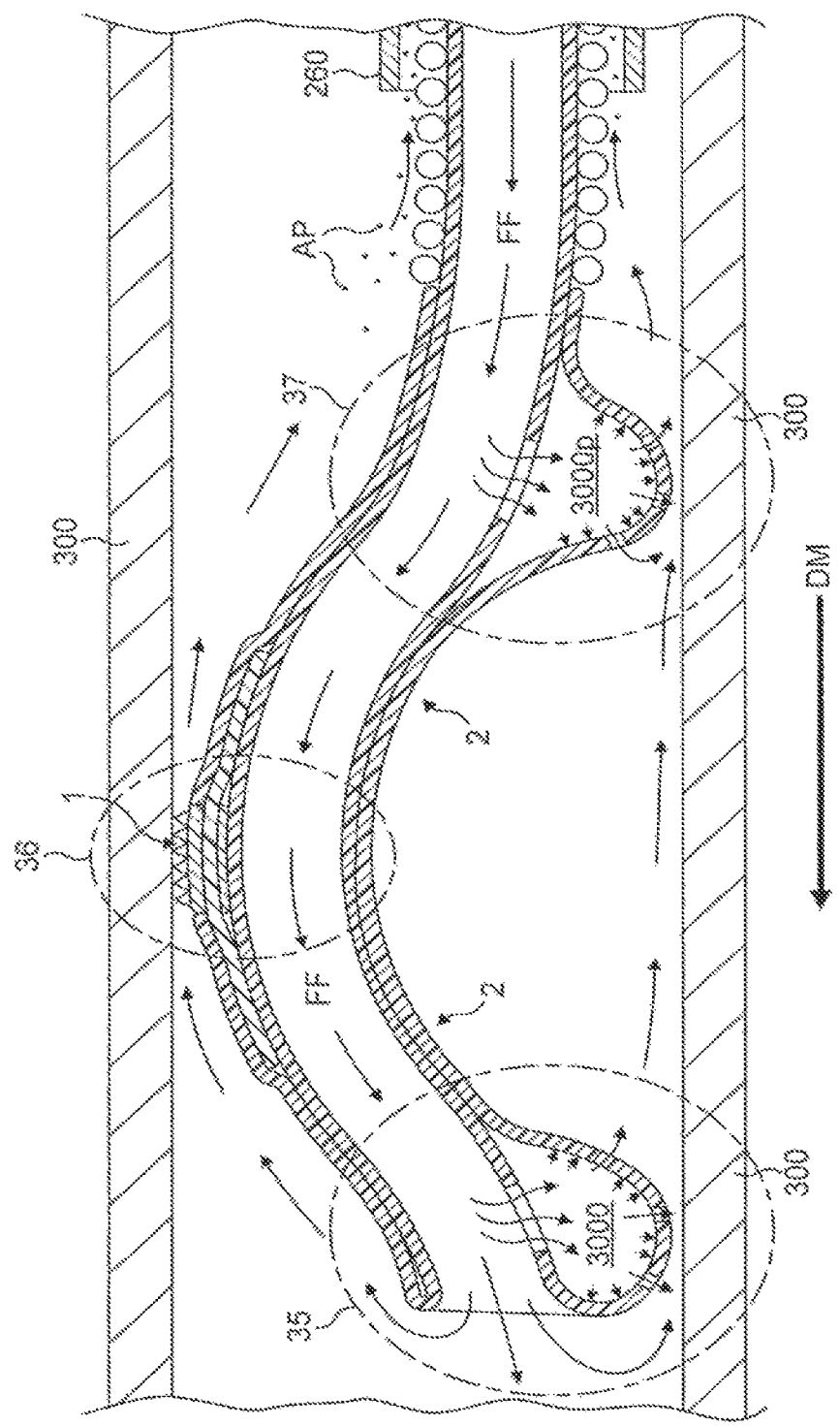
Figure 37:
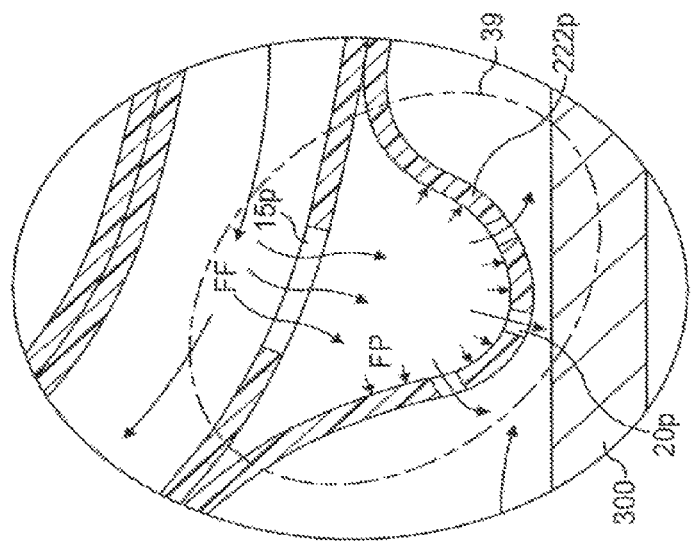
FIGS. 35 through 39 show magnified views of the abrasive element and the fluid inflatable support elements, these figures illustrating best how the flows of fluid out of the rotating fluid inflated support elements form fluid bearings between the outer walls of the rotating fluid inflated support elements and the wall of the vessel.
Figure 36:
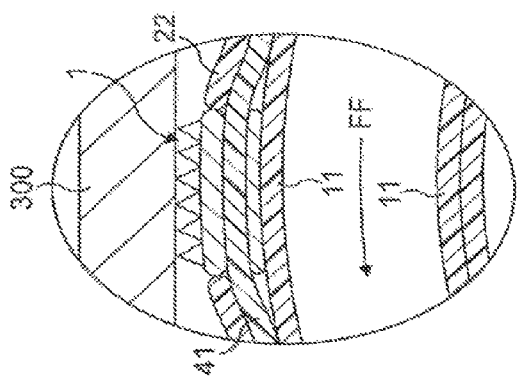
Figure 35:
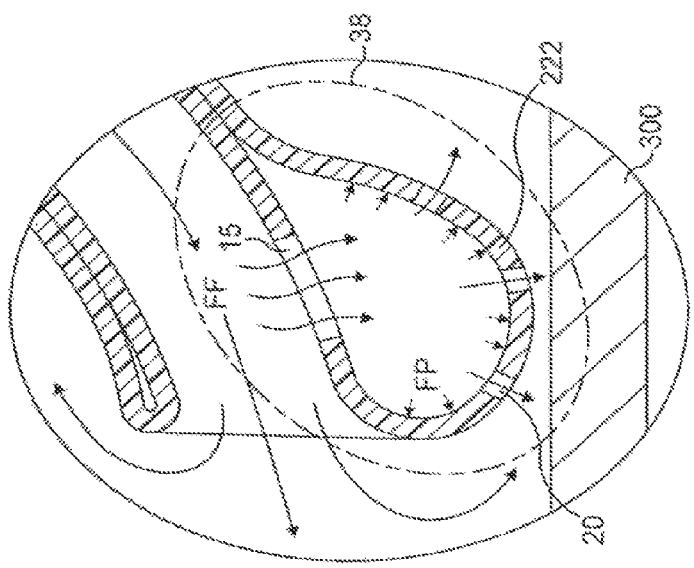
Figure 39:
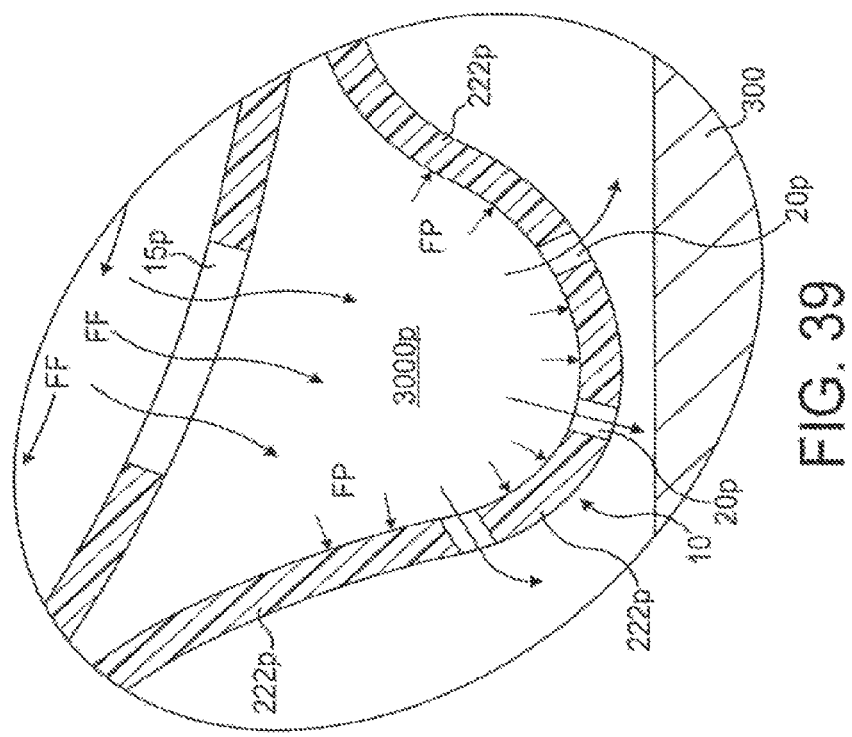

FIGS. 2, 3 and 6 illustrate best that the outer wall 222 of the distal fluid inflatable support element 10 has at least one outflow opening 20 which enables flow of fluid out of the distended fluid inflatable distal support element 10. The distal fluid inflatable support element 10 becomes distended by flow of fluid through the inflow aperture 15 in its inner wall 111. The inflow aperture 15 communicates a lumen of the fluid impermeable drive shaft 2 with an inflatable space 3000 within the distal fluid inflatable support element 10, said inflatable space 3000 is at least partially defined by a fluid impermeable membrane which forms the outer wall 222 of the distal fluid inflatable support element 10.

An area of the inflow aperture 15 through which fluid enters the distal inflatable support element 10 is larger than the total area of all the outflow opening(s) 20 through which fluid exits the distal inflatable support element 10 so that the distal fluid inflatable support element 10 is kept inflated by the pressure of the fluid flowing through the distal inflatable support element 10.

FIGS. 1, 2, 3 and 6 show the first most preferred embodiment of the invention. In this embodiment the distal fluid inflatable support element 10 is asymmetric with respect to a longitudinal axis of the drive shaft. FIGS. 2 and 6 best illustrate that, after being inflated by fluid, such asymmetric distal support element has its centre of mass CM spaced away from the longitudinal axis W-W of the drive shaft 2. FIGS. 1, 2, 4 and 7 show an abrasive element 1 which is mounted to the drive shaft 2 proximal to and spaced away from the asymmetric distal fluid inflatable support element 10. FIGS. 1, 2, 4 and 7 illustrate that the abrasive element 1 extends only around a portion of the circumference of the drive shaft 2 and therefore has its centre of mass spaced radially away from the longitudinal axis of the drive shaft. Preferably, the centre of mass CM of the asymmetric fluid inflated distal support element 10 is spaced radially away from the longitudinal axis W-W of the drive shaft in one direction and the centre of mass of the abrasive element 1 is spaced radially away from the longitudinal axis W-W of the drive shaft in another diametrically opposite direction, so that in a rotating drive shaft such asymmetric fluid inflated distal support element 10 becomes a distal fluid inflatable counterweight with respect to the abrasive element 1.

FIG. 2 illustrates that the outer wall 222 of the fluid inflated distal support element 10 is rounded and bows radially outwardly at least along its longitudinally middle section which extends in a longitudinal cross-section between an outflow opening 20 which is located longitudinally most distally within the outer wall 222 and another outflow opening 20 which is located longitudinally most proximally within the outer wall 222.

Each outflow opening 20 in the outer wall 222 of the distal fluid inflatable support element has its own axis K-K. FIG. 2 illustrates that the asymmetric distal fluid inflatable support element 10 when inflated has at least one outflow opening 20 in its longitudinally rounded outer wall 222 located such that the axis K-K of the outflow opening 20 forms an acute angle α of at least sixty (60) degrees with respect to the longitudinal axis of the drive shaft. In the first most preferred embodiment of the invention, the asymmetric distal fluid inflatable support element 10 when inflated has at least one outflow opening 20 in its outer wall 222 located such that the axis K-K of the outflow opening 20 forms an angle β of about ninety (90) degrees angle with respect to the longitudinal axis W-W of the drive shaft 2. FIGS. 15 through 26 illustrate that in the rotating asymmetric fluid inflated distal support element 10 at least one of the above described outflow openings 20 is located such that its axis K-K forms about a ninety (90) degrees angle with respect to the inner surface of the wall 300 of the treated vessel.

Figure 38:
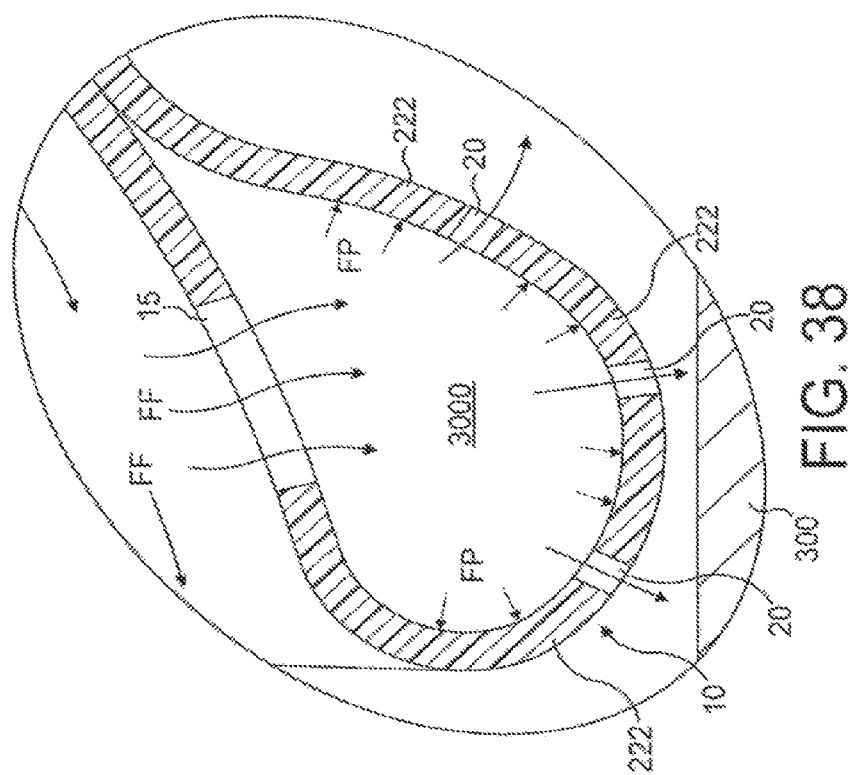

During rotation of the drive shaft, centrifugal force attempts to press a rotating asymmetric fluid inflated distal support element 10 against the wall 300 of the treated vessel, but fluid exiting from the outflow opening 20 along its axis K-K at an angle of about ninety (90) degrees with respect to the wall 300 of the vessel forms a thin layer of fluid between the outer wall 222 of the fluid inflated distal support element 10 and an inner surface of the wall 300 of the vessel. The formation of a thin layer of fluid between the outer wall 222 of the rotating fluid inflated distal support element 10 and an inner surface of the wall 300 of the vessel is best illustrated in FIG. 38. FIG. 38 shows a portion of the vascular wall 300 and a magnified view of the rotating fluid inflated distal support element 10 which has its outer wall 222 separated from the inner surface of the wall 300 by a thin layer of fluid exiting from the rotating extended distal support element 10 through outflow opening(s) 20 in its outer wall 222.

FIGS. 15 through 26 illustrate rotation of the fluid inflated distal support element 10 with the centre of mass radially spaced away from the longitudinal (rotational) axis of the drive shaft. Centrifugal force attempts to press the rotating fluid inflated distal support element 10 against the wall 300 of the vessel, but at least one outflow opening 20 in the outer wall 222 of the rotating fluid inflated distal support element 10 is located such that a flow of fluid through said outflow opening 20 forms a layer of fluid between the outer wall 222 of the rotating fluid inflated distal support element 10 and the wall 300 of the treated vessel. Preferably, the fluid inflated distal support element 10 with the centre of mass radially spaced away from the longitudinal (rotational) axis of the drive shaft should have at least one outflow opening 20 in the outer wall 222 of the distal inflatable support element 10 located such that at any time during rotation of the drive shaft 2 said outflow opening 20 is facing an inner surface of the treated vessel so that a flow of fluid through the opening 20 forms a layer of fluid between the outer wall 222 of the rotating fluid inflated distal support element 10 and the wall 300 of a treated vessel. Said layer of fluid forms a fluid bearing between the outer wall 222 of the rotating fluid inflated distal support element 10 and the wall 300 of the treated vessel.

Figure 4:
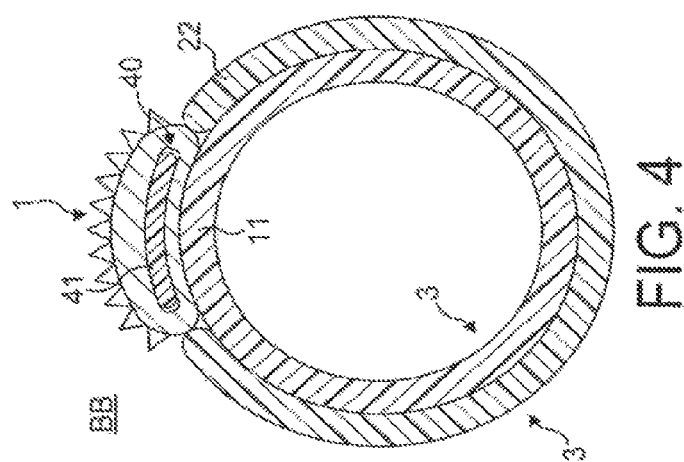
FIG. 4 is an enlarged cross-sectional view taken along a line B-B in FIG. 1 and illustrates attachment of the abrasive element to the drive shaft.
Figure 5:
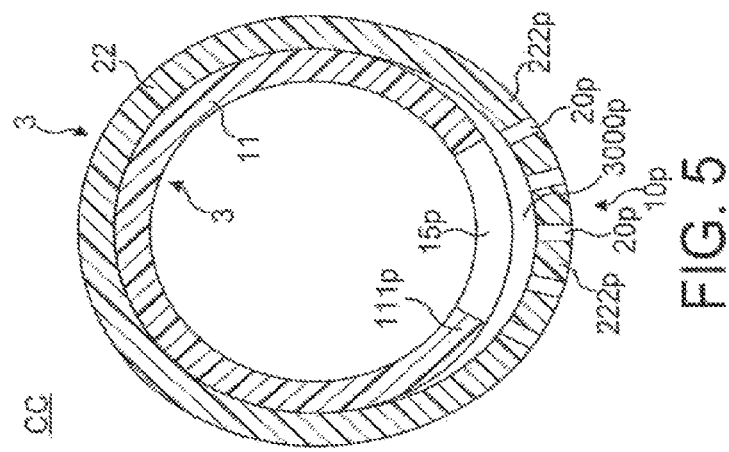
FIG. 5 shows an enlarged cross-sectional view of the proximal inflatable support element taken along a line C-C in FIG. 1.
Figure 40:
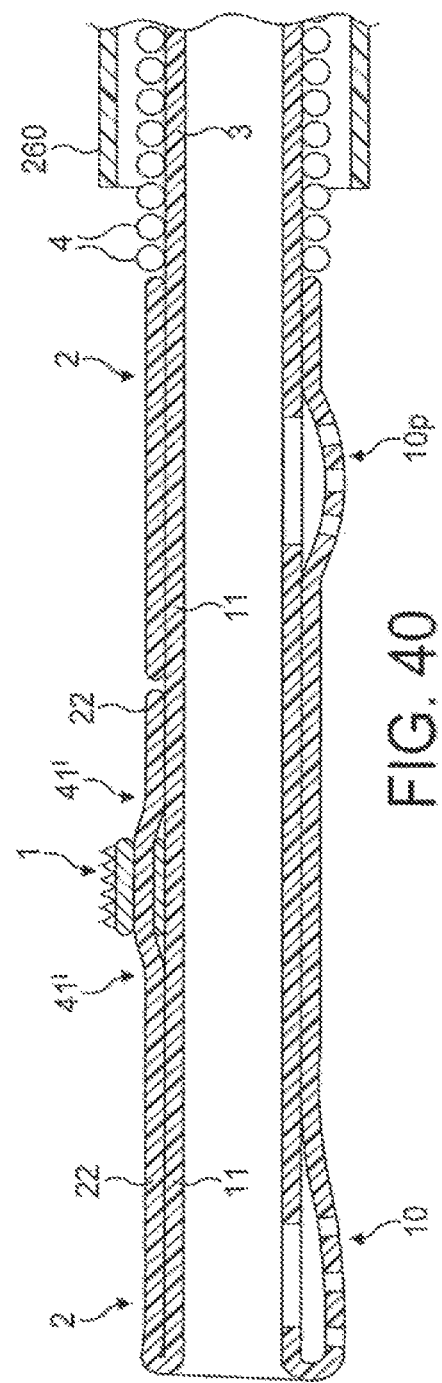
FIG. 40 is similar to FIG. 1 except that it illustrates the abrasive element being attached to the drive shaft by the longitudinally extending strap which is made integrally with the fluid impermeable membrane of the drive shaft.

FIGS. 1 and 4 show one embodiment of the invention in which the abrasive element 1 has a longitudinally extending slot 40. The abrasive element 1 is mounted to the drive shaft 2 by a flexible strap 41 which extends through said slot 40 and is bonded to the fluid impermeable membrane both distal and proximal to the abrasive element 1. Preferably, the outer layer 22 of the folded fluid impermeable membrane 3 extends proximally beyond the abrasive element 1. Preferably, in this embodiment of the invention, the flexible strap 41 which mounts the abrasive element 1 to the drive shaft 2 extends between the inner 11 and outer 22 layers of the folded fluid impermeable membrane 3 both distal and proximal to the abrasive element 1. In such an embodiment, the outer layer 22 of the folded fluid impermeable membrane 3 has an opening through which an abrasive surface of the abrasive element 1 protrudes above a surface of the outer layer 22 of the folded fluid impermeable membrane. FIG. 40 shows one variation of the invention in which longitudinally extending strap 41' is formed integrally with the outer layer 22 of the folded fluid impermeable membrane 3. FIG. 40 illustrates that in such embodiment the longitudinally extending strap 41' is continuous with the outer layer 22 of the folded fluid impermeable membrane 3 distally to the abrasive element 1 and is bonded to the fluid impermeable membrane 3 proximally to the abrasive element 1.

Figure 41:
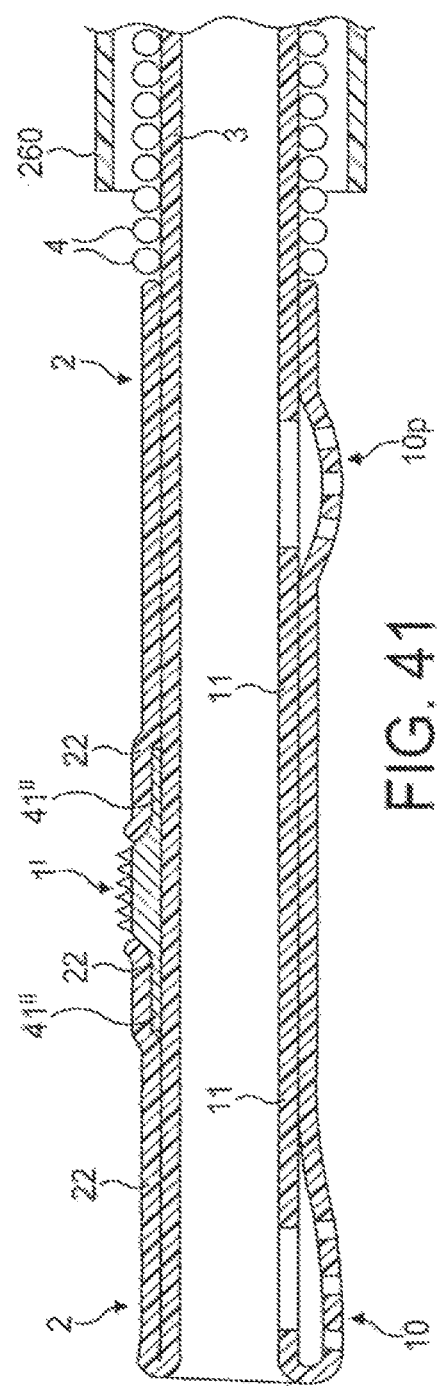
FIG. 41 is similar to FIG. 1 except that it illustrates the abrasive element being made integrally with the longitudinally extending strap which attaches the abrasive element to the drive shaft.
Figure 42:
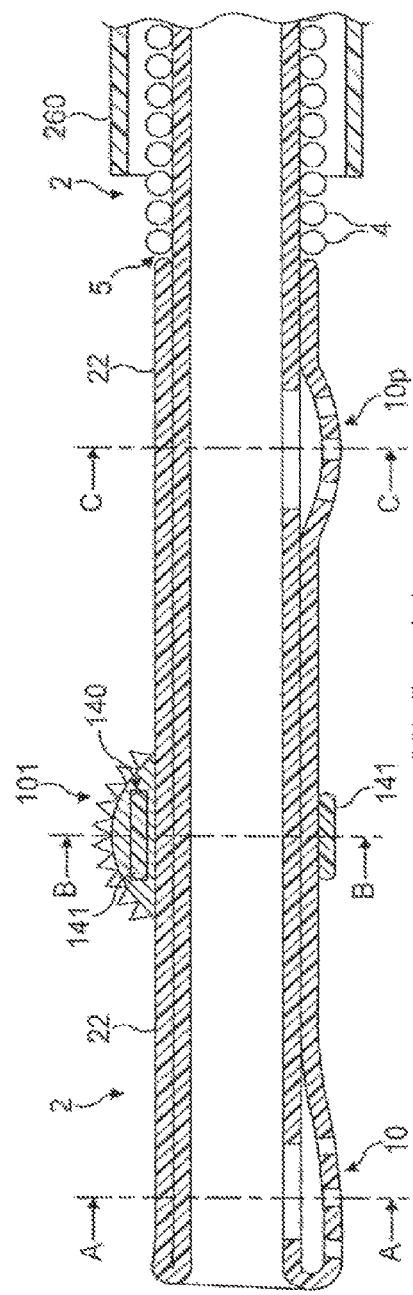
Figure 43:
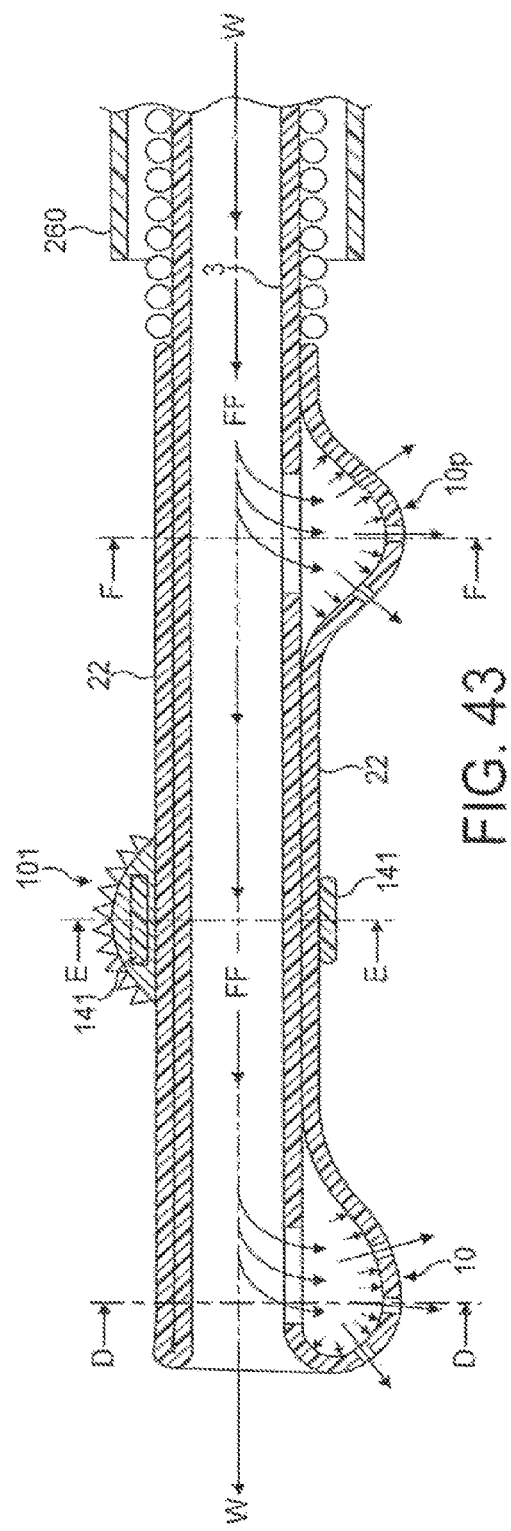
Figure 49:
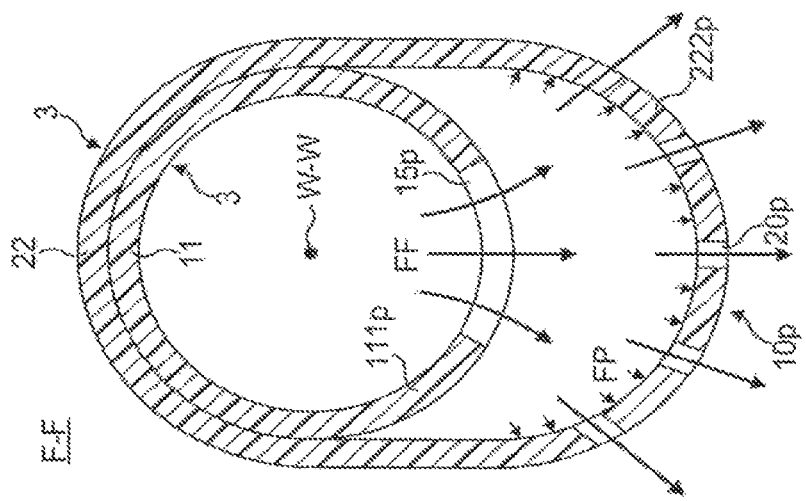
Figure 48:
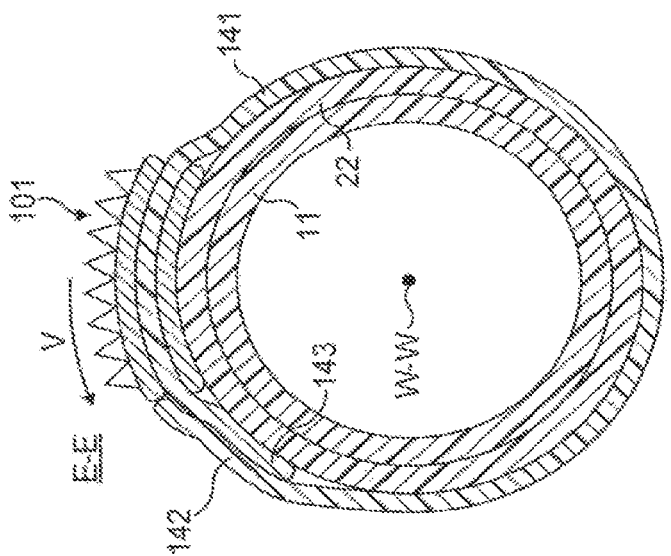
Figure 47:
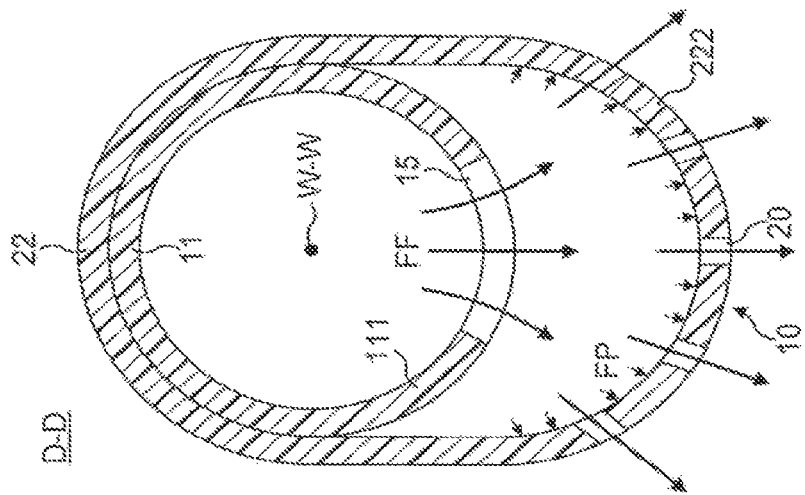

FIG. 41 shows another variation of the invention in which the abrasive element 1' is formed integrally with the longitudinally extending strap 41". Both the body of the abrasive element and the longitudinally extending strap in such embodiment may be made from sufficiently flexible material such as gold, the longitudinally extending strap being made substantially thinner than the body of the abrasive element in order to make the strap sufficiently flexible. It should be noted that the rotational atherectomy devices with abrasive elements which do not extend around the entire circumference of the drive shaft may have advantages for crossing and abrading tight stenotic lesions. Therefore, any abrasive element which is attached to the drive shaft by a longitudinally extending strap should extend around less than a half of the circumference of the drive shaft and preferably even around less than a third of the circumference of the drive shaft.

In yet another variation of the first embodiment of the invention shown in FIGS. 42 through 49, the abrasive element 101 has a transverse extending slot 140 and is mounted to the drive shaft 2 by a flexible strap 141 which extends through said slot and is wrapped around the drive shaft 2. Preferably, in this embodiment the flexible strap 141 is wrapped around the fluid impermeable membrane 3 distal to the distal end 5 of the torque transmitting coil 4. In the preferred embodiment the flexible strap 141 is wrapped around the outer layer 22 of the folded fluid impermeable membrane. FIG. 45 illustrates that the flexible strap 141 has leading and trailing edge portions relative to the direction (arrow V) of rotation of the drive shaft 2, the trailing edge portion 142 of the flexible strap 141 extends around the drive shaft and at least partially overlaps the leading edge portion 143 of said strap 141. The overlapping trailing 142 and leading 143 edge portions of the flexible strap 141 are preferably bonded to each other. The abrasive element 101 also has a rotationally leading edge 801 and a rotationally trailing edge 802 relative to the direction of rotation of the drive shaft 2.

Figure 56:
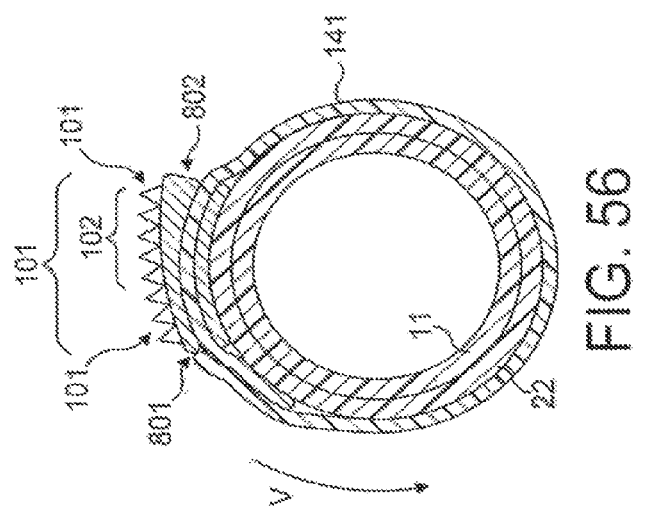
FIG. 56 illustrates in a transverse cross-section an abrasive element which has its rotationally trailing edge made thicker than its rotationally leading edge.

FIG. 56 shows that the rotationally leading edge 801 of the abrasive element 101 is made thinner than its trailing edge 802 so that during rotation of the drive shaft an abrasive surface 10001 of the abrasive element 101 may engage and abrade stenotic tissue only by a thicker portion of the abrasive element 101, said thicker portion 10002 of the abrasive element being spaced away from the leading edge 801 of the abrasive element 101. The abrasive element with a thinner leading edge 801 and thicker trailing edge 802 allows to gradually increase the degree of engagement of the abrasive surface 10001 of the abrasive element 101 with the stenotic tissue to be abraded. It should be noted that variation of the abrasive element shown in FIG. 56 may be used with any embodiment of the rotational atherectomy device of the invention.

It should be noted that the rotational atherectomy devices with abrasive elements which do not extend around the entire circumference of the drive shaft may have advantages for crossing and abrading tight stenotic lesions. Preferably, abrasive elements which are attached to the drive shaft by straps should extend around less than a half of the circumference of the drive shaft. The abrasive elements which extend around less than a third of the circumference of the drive shaft may allow the crossing and abrading of very tight stenotic lesions even when they are attached to the drive shaft by the straps which extend around the entire circumference of the drive shaft.

Figure 8:
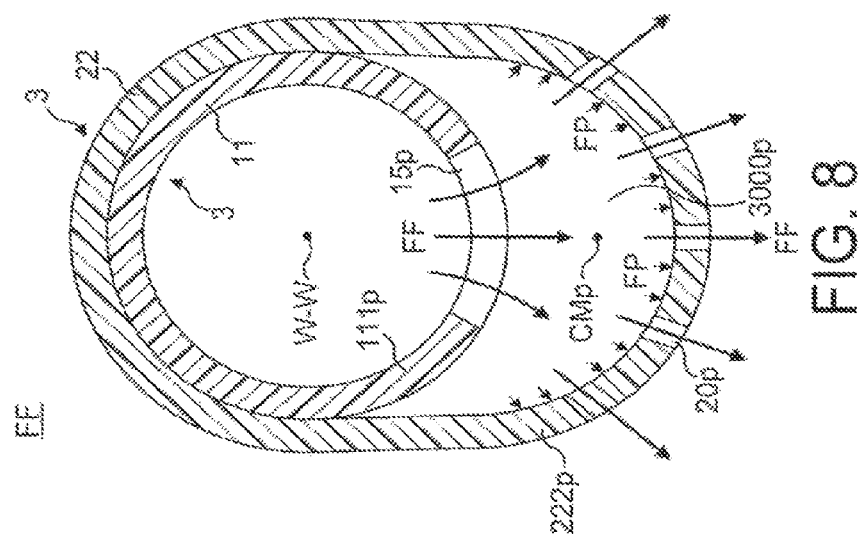
FIG. 8 shows an enlarged cross-sectional view taken along a line F-F in FIG. 2 and illustrates flow of fluid into and out of the proximal fluid inflated support element.
Figure 7:
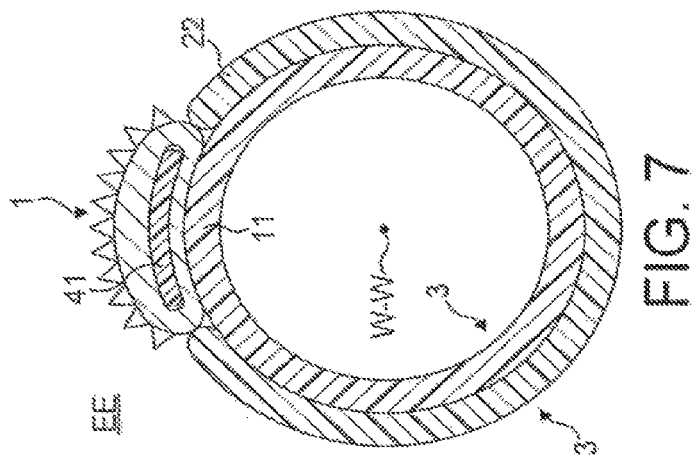
FIG. 7 is similar to FIG. 4 except that it is taken along a line E-E in FIG. 2.

It should be noted that in the most preferred embodiments of the invention, the fluid impermeable drive shaft is provided with two fluid inflatable support elements, one located at the distal end of the drive shaft and the other proximal to and spaced away from the abrasive element. FIGS. 1 through 8 illustrate the first most important embodiment of the invention in which the drive shaft 2 is provided with both a distal fluid inflatable support element 10 and a proximal fluid inflatable support element 10p, both the distal and the proximal support elements 10,10p being asymmetric with respect to the longitudinal axis of the drive shaft 2. The proximal fluid inflatable support element 10p has an inner wall 111p and an outer wall 222p. In the first most preferred embodiment of the invention, the outer wall 222p of the proximal fluid inflatable support element 10p is formed by the outer layer 22 of the folded fluid impermeable membrane 3. The inner wall 111p of the proximal fluid inflatable support element 10p is formed by the inner layer 11 of the folded fluid impermeable membrane 3. The inner wall 111p of the proximal fluid inflatable support element 10p has an inflow opening (aperture) 15p therein. FIGS. 2 and 8 illustrate that a portion of flushing fluid FF flowing in an antegrade direction along the drive shaft 2 is redirected through the inflow opening (aperture) 15p into the proximal inflatable support element 10p to inflate said proximal inflatable support element. FIG. 2 illustrates best that in order to form the proximal fluid inflatable support element 10p, the inner 11 and outer 22 layers of the folded fluid impermeable membrane 3 are connected or bonded to each other at least just distal and proximal to the proximal fluid inflatable support element 10p. In this location, just distal and proximal to the proximal fluid inflatable support element 10p, the inner 11 and the outer 22 layers of the membrane 3 are preferably connected or bonded to each other around the entire circumference of the drive shaft 2.

Figure 57:
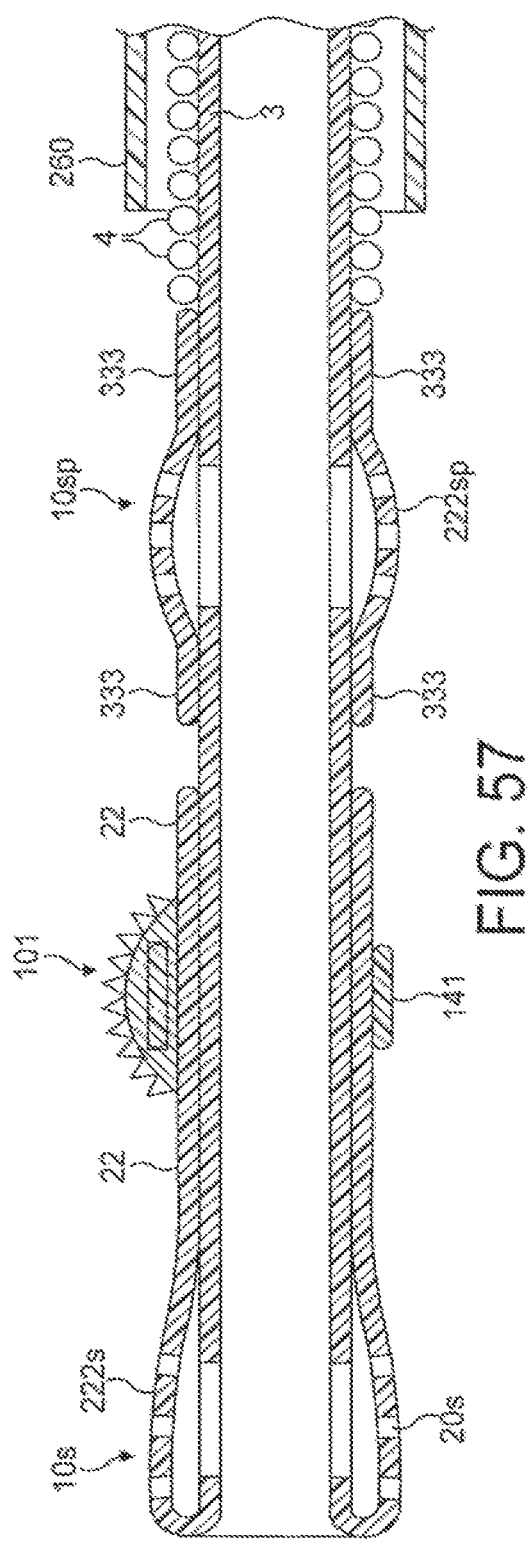
FIG. 57 illustrates the drive shaft which has the outer wall of its proximal fluid inflatable support element formed by a membrane which is not continuous with the membrane which forms the outer wall of the distal fluid inflatable support element.
Figure 60:
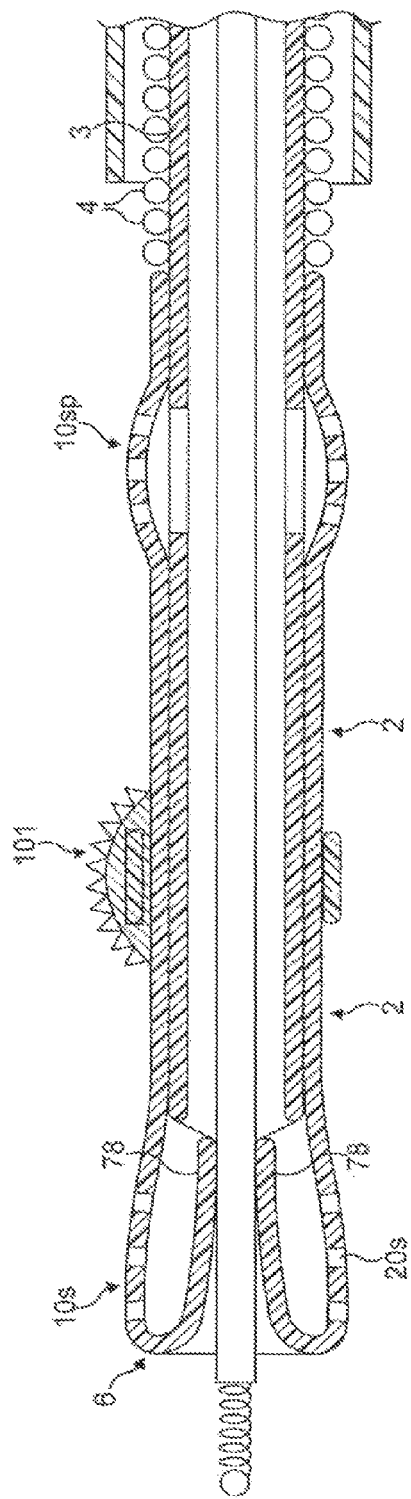
FIGS. 60 and 61 show a flexible leaf valve formed at the distal end of the drive shaft with symmetric fluid inflatable support elements, said flexible leaf valve having one or more leaflets.
Figure 61:
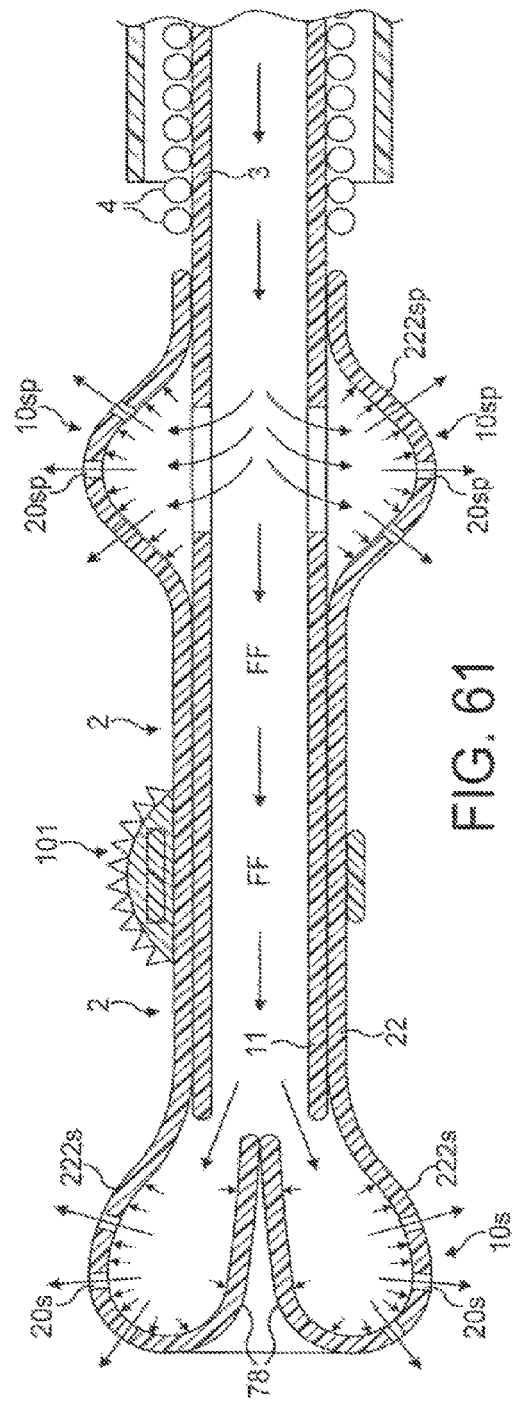

It should be noted that in either of the two most preferred embodiments of the invention, the outer wall of the proximal fluid inflatable support element may be formed not only by a proximal portion of the outer layer 22 of the folded fluid impermeable membrane 3, but by a separate fluid impermeable membrane 333 shown in FIG. 57. The separate fluid impermeable membrane 333 should be bonded circumferentially to the fluid impermeable membrane 3 at least just distal and proximal to the proximal fluid inflatable support element.

The following discussion is focused on the design and function of the proximal fluid inflatable support element 10p which has its outer wall 222p formed by the outer layer 22 of the folded fluid impermeable membrane 3, but it should be understood that the same discussion would be applicable to a proximal fluid inflatable support element which has its outer wall formed by the separate fluid impermeable membrane 333 shown in FIG. 57. The following discussion is particularly applicable with respect to the location and function of openings in the outer wall of the proximal fluid inflatable support element.

In the preferred embodiments of the invention, the outer wall 222p of the proximal fluid inflatable support element 10p has at least one outflow opening 20p which enables flow of fluid out of the distended fluid inflatable proximal support element 10p. The proximal fluid inflatable support element 10p becomes distended by flow of fluid through its inflow aperture 15p which communicates the lumen of the fluid impermeable drive shaft 2 with the inflatable space 3000p within the proximal fluid inflatable support element 10p. The fluid inflatable space 3000p is at least partially defined by a fluid impermeable membrane which forms an outer wall 222p of the proximal fluid inflatable support element 10p.

An area of the inflow aperture 15p through which fluid enters the proximal inflatable support element 10p is larger than the area of the outflow opening(s) 20p through which fluid exits the proximal inflatable support element 10p so that the proximal fluid inflatable support element 10p is kept inflated by the pressure of the fluid flowing through the proximal inflatable support element 10p.

FIGS. 1, 2, 5 and 8 show the proximal fluid inflatable support element 10p which is asymmetric with respect to a longitudinal axis of the drive shaft 2. FIGS. 1, 2, 5 and 8 show that, after being inflated by fluid, such asymmetric proximal support element 10p has its centre of mass CMp spaced away from the longitudinal axis W-W of the drive shaft 2. FIGS. 1, 2, 4 and 7 show best an abrasive element 1 which is mounted to the drive shaft 2 distal to and spaced away from the asymmetric proximal fluid inflatable support element 10p. As previously mentioned, the abrasive element 1 extends only around a portion of the circumference of the drive shaft 2 and therefore has its centre of mass spaced radially away from the longitudinal axis W-W of the drive shaft 2. Preferably, the centre of mass CMp of the asymmetric fluid inflated proximal support element 10p is spaced radially away from the longitudinal axis W-W of the drive shaft in one direction and the centre of mass of the abrasive element 1 is spaced radially away from the longitudinal axis W-W of the drive shaft 2 in another diametrically opposite direction, so that in a rotating drive shaft such asymmetric fluid inflated proximal support element 10p forms (acts as) a proximal fluid inflatable counterweight with respect to the abrasive element 1.

FIG. 2 illustrates that the outer wall 222p of the fluid inflated proximal support element 10p is bowing longitudinally outwards at least along its longitudinally middle section which extends in a longitudinal cross-section between an outflow opening 20p which is located longitudinally most distally within the outer wall 222p and another outflow opening 20p which is located longitudinally most proximally within the outer wall 222p.

Each outflow opening 20p in the outer wall 222p of the proximal fluid inflatable support element has its own axis L-L. FIG. 2 illustrates that the asymmetric proximal fluid inflatable support element 10p when inflated has at least one outflow opening 20p in its outer wall 222p located such that the axis L-L of the outflow opening 20p forms an acute angle α of at least sixty (60) degrees with respect to the longitudinal axis W-W of the drive shaft 2. In the most preferred embodiment of the invention, the asymmetric proximal fluid inflatable support element 10p when inflated has at least one outflow opening 20p in its outer wall 222p located such that the axis L-L of the outflow opening 20p forms about a ninety (90) degrees angle β with respect to the longitudinal axis of the drive shaft 2.

FIGS. 15 through 26 illustrate that in the rotating asymmetric fluid inflated proximal support element 10p at least one of the above described outflow openings 20p is located such that its axis L-L forms about a ninety (90) degrees angle with respect to the inner surface of the wall 300 of the treated vessel. Centrifugal force attempts to press a rotating asymmetric fluid inflated proximal support element 10p against the wall 300 of the treated vessel, but fluid exiting from the outflow opening 20p along its axis L-L at an angle of about ninety (90) degrees with respect to the wall 300 of the vessel forms a thin layer of fluid between the rounded outer wall 222p of the fluid inflated proximal support element 10p and an inner surface of the wall 300 of the vessel. The asymmetric fluid inflated proximal support element 10p has its centre of mass spaced radially away from the longitudinal (rotational) axis of the drive shaft. Centrifugal force attempts to press the rotating fluid inflated proximal support element 10p against the wall 300 of the vessel, but at least one outflow opening 20p in the longitudinally rounded outer wall 222p of said rotating fluid inflated proximal support element 10p is located such that a flow of fluid through said opening 222p forms a layer of fluid between the outer wall 222p of the rotating fluid inflated proximal support element 10p and the wall 300 of the treated vessel. Preferably, the fluid inflated proximal support element 10p with the centre of mass radially spaced away from the longitudinal (rotational) axis of the drive shaft 2 should have at least one outflow opening 20p in the longitudinally rounded outer wall 222p of the proximal inflatable support element 10p located such that at any time during rotation of the drive shaft 2 said outflow opening 20p is facing an inner surface of the treated vessel so that a flow of fluid through the outflow opening 20p forms a layer of fluid between the longitudinally rounded outer wall 222p of the rotating fluid inflated proximal support element 10p and the wall 300 of a treated vessel. Said layer of fluid forms a fluid bearing between the outer wall 222p of the rotating fluid inflated proximal support element 10p and the wall 300 of the treated vessel.

FIGS. 50 and 51 illustrate the second most preferred embodiment of the distal end portion of the rotational atherectomy device of the invention. In this second most preferred embodiment, the distal fluid inflatable support element 10s is symmetric with respect to a longitudinal axis W-W of the drive shaft. This symmetric distal fluid inflatable support element 10s has a fluid inflatable space 3000s which extends uniformly around the drive shaft 2, so that after being inflated by fluid the distal support element 10s has its centre of mass coaxial with the longitudinal axis W-W of the drive shaft 2. An inflow opening (aperture) 15s communicates the fluid inflatable space 3000s within the inflatable support element 10s with the lumen of the fluid impermeable drive shaft 2. The fluid inflatable space 3000s is defined by a fluid impermeable membrane which forms at least a portion of the wall 222s of the symmetric distal fluid inflatable support element 10s.

FIG. 51 illustrates in a longitudinal cross-section that the symmetric distal fluid inflatable support element has a maximum diameter circumference when inflated and that the outer wall 222s of the fluid inflated symmetric distal support element 10s is bowing longitudinally outward at least along the maximum diameter circumference of the inflated symmetric distal support element.

The outer wall 222s of the symmetric distal fluid inflatable support element 10s has at least one outflow opening 20s. Preferably, the symmetric distal fluid inflatable support element 10s has a plurality of outflow openings 20s in its outer wall 222s. Each outflow opening 20s in the outer wall 222s of the symmetric distal fluid inflatable support element 10s has its own axis M-M. FIG. 51 illustrates that the symmetric distal fluid inflatable support element 10s when inflated has at least one outflow opening 20s in its outer wall 222s located such that the axis M-M of the outflow opening 20s forms an acute angle α of at least sixty (60) degrees with respect to the longitudinal axis W-W of the drive shaft 2. In the second most preferred embodiment of the invention, the symmetric distal fluid inflatable support element 10s when inflated has at least one outflow opening 20s in its outer wall 222s located such that the axis M-M of the outflow opening 20s forms about a ninety (90) degrees angle β with respect to the longitudinal axis W-W of the drive shaft. FIGS. 52 through 55 illustrate that in the rotating symmetric fluid inflated distal support element 10s at least one of the above described outflow openings 20s is located such that its axis M-M forms about a ninety (90) degrees angle with respect to the inner surface of the wall 300 of the treated vessel. FIGS. 52 through 55 also illustrate that in a curved vessel the drive shaft 2 attempts to maintain its straight configuration and therefore attempts to press a rotating symmetric distal fluid inflated support element 10s against the outer curvature of the vessel but fluid exiting from the outflow opening 20s along its axis M-M at an angle of about ninety (90) degrees with respect to the wall 300 of the vessel forms a thin layer of fluid between the outer wall 222s of the fluid inflated distal support element 10s and the inner surface of the outer curvature of the wall 300 of the treated vessel.

Preferably, the fluid inflated symmetric distal support element 10s should have a plurality of outflow openings 20s located around the circumference of the outer wall 222s, the outflow openings 20s located in a longitudinally bowing outward segment of the outer wall 222s such that at any time during rotation of the drive shaft 2 at least one of these outflow openings 20s is facing an inner surface of the treated vessel so that a flow of fluid through the outflow opening 20s forms a layer of fluid between the outer wall 222s of the rotating fluid inflated symmetric distal support element 10s and the wall 300 of the treated vessel. Said layer of fluid forms a fluid bearing between the outer wall 222s of the rotating fluid inflated distal support element 10s and the wall 300 of the treated vessel.

It should be noted that in the second most preferred embodiments of the invention, the fluid impermeable drive shaft is provided with two symmetric fluid inflatable support elements, one located at the distal end of the drive shaft and the other proximal to and spaced away from the abrasive element. FIGS. 50 and 51 illustrate the second most preferred embodiment of the invention in which the drive shaft 2 is provided with both a symmetric distal fluid inflatable support element 10s and a symmetric proximal fluid inflatable support element 10sp. The symmetric proximal fluid inflatable support element 10sp has an inner wall 111sp and an outer wall 222sp. In the preferred embodiment of the invention, the outer wall 222sp of the symmetric proximal fluid inflatable support element 10sp is formed by the outer layer 22 of the folded fluid impermeable membrane 3. The inner wall 111sp of the symmetric proximal fluid inflatable support element 10sp is formed by the inner layer 11 of the folded fluid impermeable membrane 3. The inner wall 111sp of the symmetric proximal fluid inflatable support element 10sp has an inflow opening (aperture) 15sp therein. This inflow opening (aperture) 15sp communicates the lumen of the fluid impermeable drive shaft 2 with an inflatable space 3000sp within the symmetric proximal fluid inflatable support element 10sp. The inflatable space 3000sp is at least partially defined by a fluid impermeable membrane which forms the outer wall 222sp of the symmetric proximal fluid inflatable support element 10sp. FIG. 51 illustrates that a portion of flushing fluid FF flowing in an antegrade direction along the drive shaft 2 is redirected through the inflow opening (aperture) 15sp into the symmetric proximal fluid inflatable support element 10sp to inflate said support element 10sp. FIG. 51 illustrates best that in order to form the symmetric proximal fluid inflatable support element 10sp, the inner 11 and outer 22 layers of the folded fluid impermeable membrane 3 are connected or bonded to each other at least just distal and proximal to the symmetric proximal fluid inflatable support element 10sp. In this location, just distal and proximal to the symmetric proximal fluid inflatable support element 10sp, the inner 11 and the outer 22 layers of the membrane 3 are preferably connected or bonded to each other around the entire circumference of the drive shaft 2.

Figure 52:
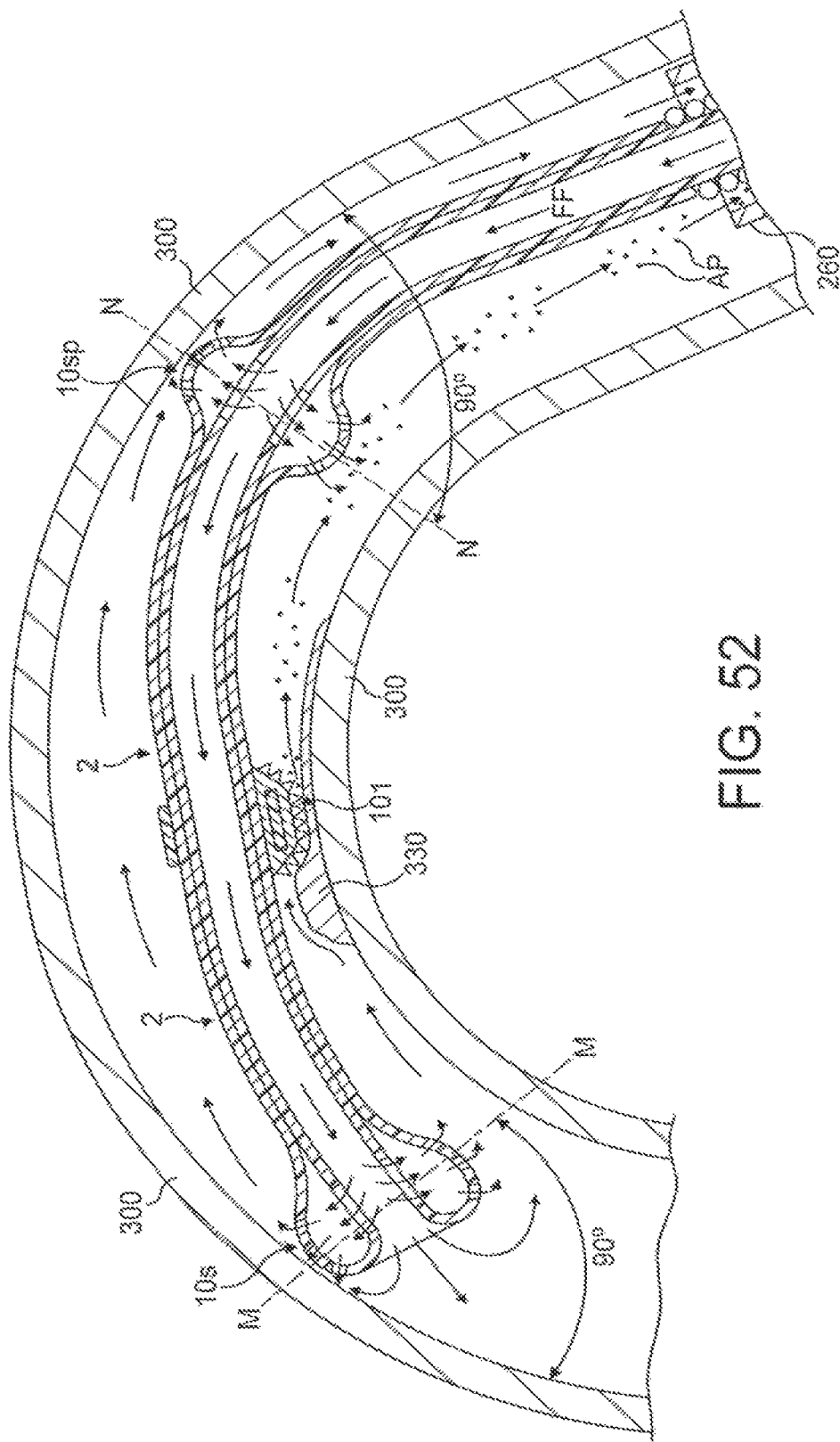
FIGS. 52 through 55 illustrate the formation of fluid bearings between the inner surface of the treated vessel and the outer walls of the rotating fluid inflated support elements, each of the support elements having fluid inflatable space which extends circumferentially around the entire circumference of the drive shaft so that, in a curved vessel, said support elements bias the abrasive element towards the inner curvature of the curved vessel and allow preferential removal of stenotic tissue from the inner curvature of the treated curved vessel.
Figure 53:
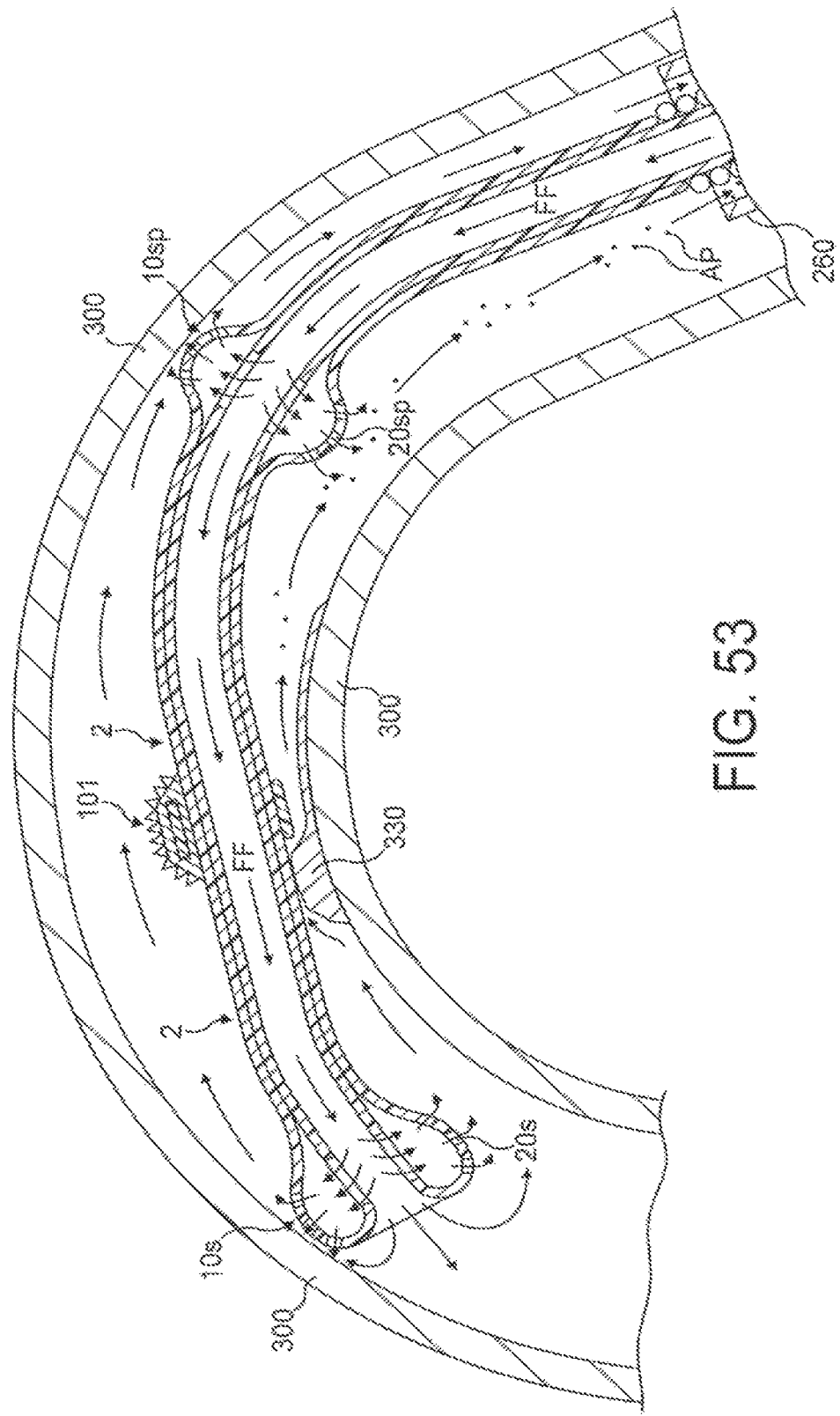
Figure 54:
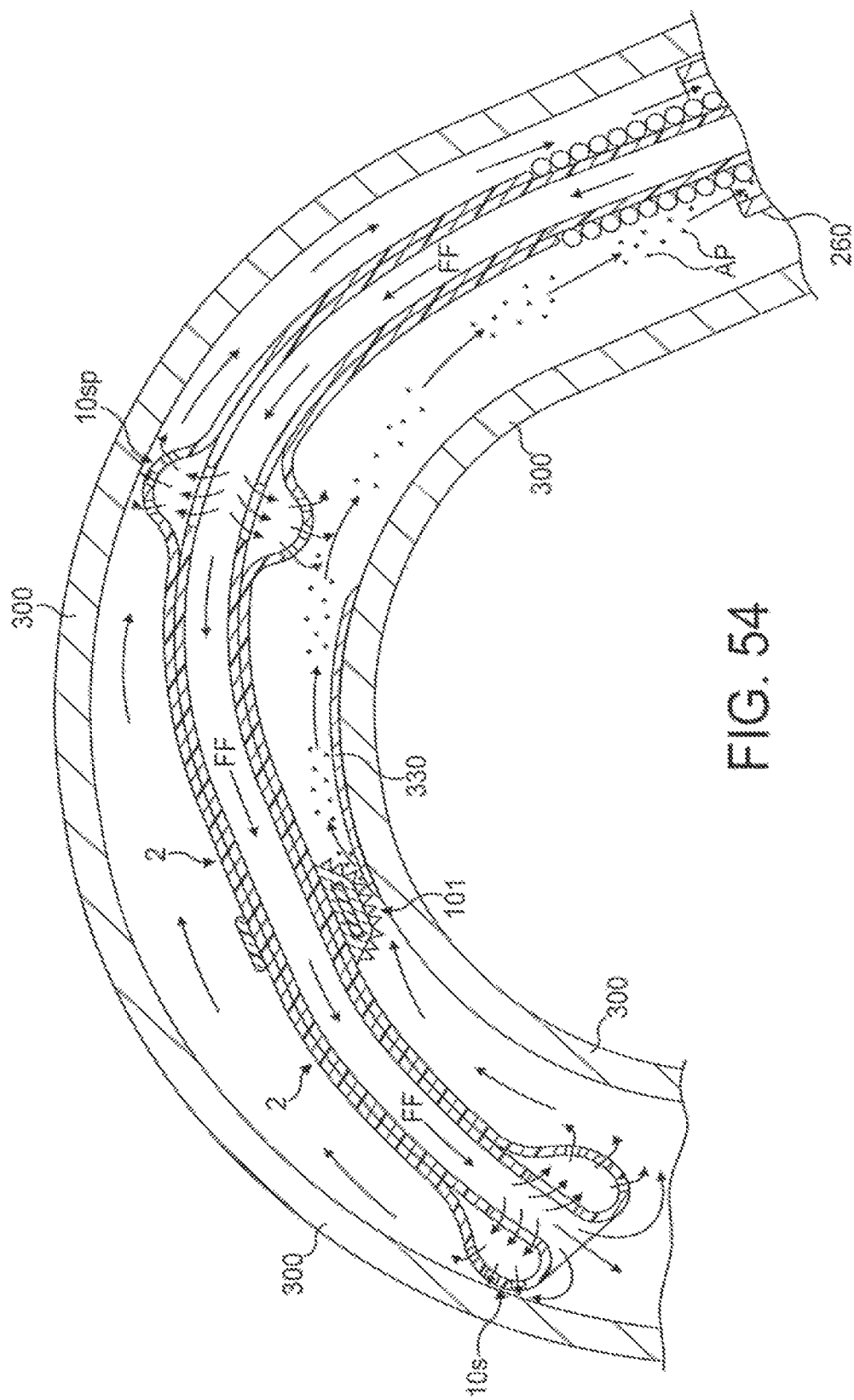
Figure 55:
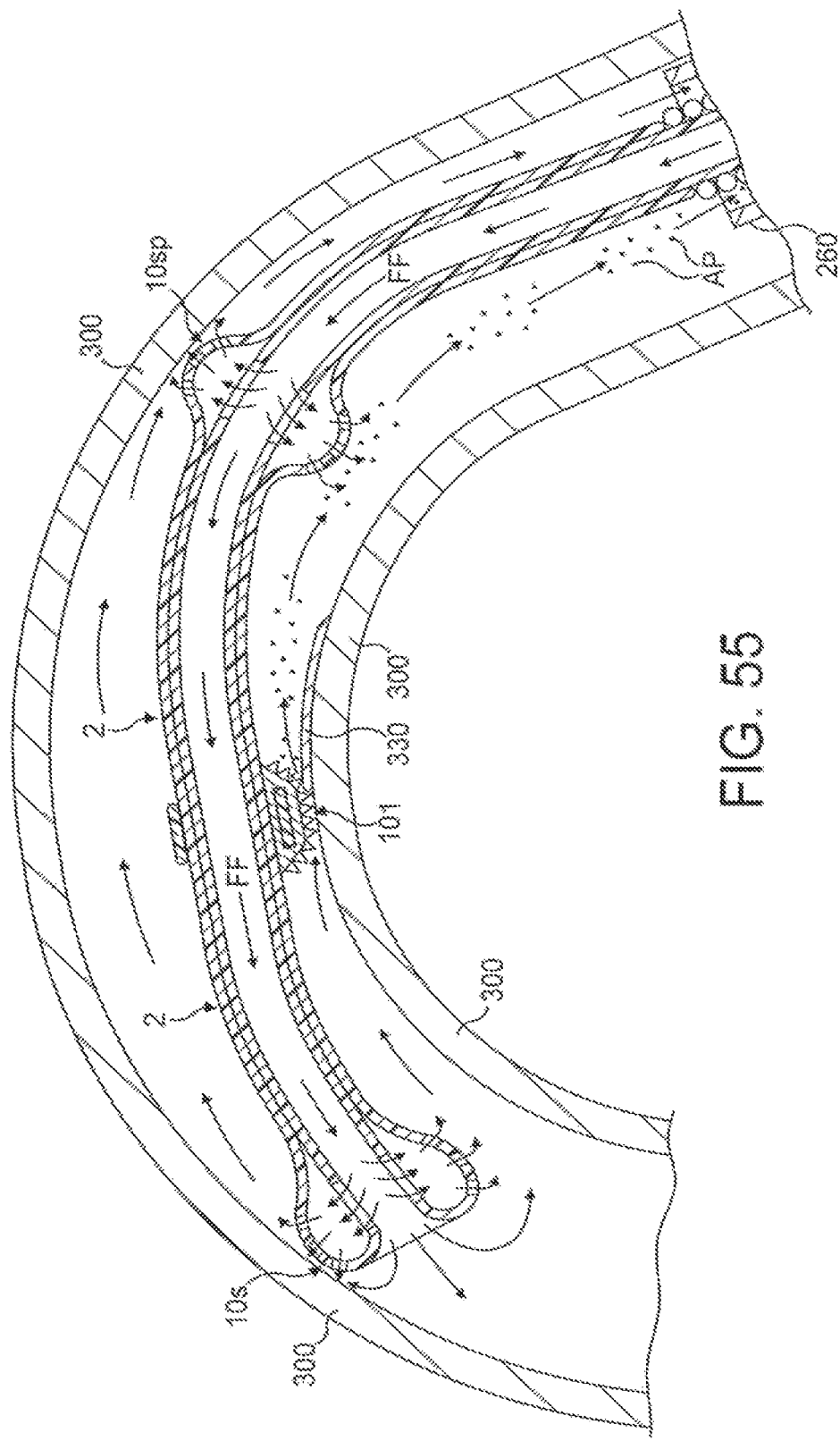

The outer wall 222sp of the symmetric proximal fluid inflatable support element 10sp has at least one outflow opening 20sp. The symmetric proximal fluid inflatable support element 10sp preferably has a plurality of outflow openings 20sp in its outer wall 222sp. Each outflow opening 20sp in the outer wall 222sp of the symmetric proximal fluid inflatable support element 10sp has its own axis N-N. FIG. 52 illustrates that the symmetric proximal fluid inflatable support element 10sp when inflated has at least one outflow opening 20sp in its outer wall 222sp located such that the axis N-N of the outflow opening 20sp forms an acute angle α of at least sixty (60) degrees with respect to the longitudinal axis W-W of the drive shaft. In the second most preferred embodiment of the invention, the symmetric proximal fluid inflatable support element 10sp when inflated has at least one outflow opening 20sp in its outer wall 222sp located such that the axis N-N of the outflow opening 20sp forms about a ninety (90) degrees angle β with respect to the longitudinal axis W-W of the drive shaft 2.

FIGS. 52 through 55 illustrate that in the rotating symmetric fluid inflated proximal support element 10sp at least one of the above described outflow openings 20sp is located such that its axis N-N forms about a ninety (90) degrees angle with respect to the inner surface of the wall 300 of the treated vessel. FIGS. 52 through 55 also illustrate that in a curved vessel the drive shaft 2 attempts to maintain its straight configuration and therefore attempts to press the rotating symmetric proximal fluid inflated support element 10sp against the outer curvature of the vessel but fluid exiting from the outflow opening 20sp along its axis N-N at an angle of about ninety (90) degrees with respect to the wall 300 of the vessel forms a thin layer of fluid between the outer wall 222sp of the fluid inflated proximal support element 10sp and an inner surface of the wall 300 of the vessel.

Preferably, the fluid inflated symmetric proximal support element 10sp should have a plurality of outflow openings 20sp spaced about equally around the circumference of the outer wall 222sp, the openings located such that at any time during rotation of the drive shaft 2 at least one of these outflow openings 20sp is facing an inner surface of the treated vessel so that a flow of fluid through the outflow opening 20sp forms a layer of fluid between the outer wall 222sp of the rotating fluid inflated symmetric proximal support element 10sp and the wall 300 of the treated vessel. Said layer of fluid forms a fluid bearing between the outer wall 222sp of the rotating fluid inflated proximal support element 10sp and the wall 300 of the treated vessel.

FIGS. 52 through 55 illustrate the formation of fluid bearings between the inner surface of the treated vessel and the outer walls of the rotating fluid inflated support elements, each of the support elements having fluid inflatable space which extends circumferentially around the entire circumference of the drive shaft so that, in a curved vessel said support elements bias the abrasive element towards the inner curvature of the curved vessel and allow preferential removal of stenotic tissue from the inner curvature of the treated curved vessel. However, it should be noted that the fluid inflatable support elements with fluid inflatable spaces which extend circumferentially around the entire circumference of the drive shaft may also be used successfully in a straight vessel where said elements, when supported by fluid bearings, allow safe rotation of the drive shaft within the treated vessel even after the guidewire has been removed from the rotational atherectomy device. The rotational atherectomy device with symmetric fluid inflatable support elements preferably comprises either an eccentric abrasive element with a centre of mass spaced away from the longitudinal axis of the drive shaft or, an abrasive element which is capable of being magnetically biased in any direction with respect to circumference of the treated vessel.

It should be noted that the outer wall 222sp of the symmetric proximal fluid inflatable support element 10sp may be formed not only by a proximal portion of the outer layer 22 of the folded fluid impermeable membrane 3, but by another fluid impermeable membrane. It should be noted that the distal end portion of the device which comprises fluid inflatable support elements can be manufactured separately to the rest of the device using methods such as injection moulding or insertion moulding, thereby eliminating need to turn the fluid impermeable membrane back on itself.

It should be noted that a non-stretchable membrane should extend around the drive shaft between the fluid inflatable elements when such elements are formed from a fluid stretchable membrane.

FIG. 64 shows a rotational atherectomy device with symmetric fluid inflatable support elements which are formed integrally with a fluid impermeable membrane without folding the membrane on itself at the distal end of the drive shaft but instead making said inflatable support elements integral with the membrane by using manufacturing methods of injection molding, insertion molding or other currently available progressive manufacturing methods. It should be understood that similar progressive manufacturing methods may be used in producing a rotational atherectomy device with asymmetric fluid inflatable support elements.

It should be noted that any of the above discussions with respect to the configuration of the abrasive element and its attachment to the drive shaft with asymmetric fluid inflatable support element(s) are also relevant with respect to the drive shaft with symmetric fluid inflatable support element(s). It also should be noted that similar progressive manufacturing methods may be used in producing a rotational atherectomy device with asymmetric fluid inflatable support elements. The abrasive elements and their fixations to the drive shaft known from WO 2006/126076 and other sources, may be used with any of the above described embodiments of this invention.

Many modifications and variations falling within the terms of the following claims will be apparent to those skilled in the art and the foregoing description should be regarded as a description of the preferred embodiments only.

The invention claimed is:

1. A rotational atherectomy device for removing a stenotic lesion from a body vessel, the device comprising:
a rotatable, flexible drive shaft comprising a torque transmitting coil and at least one fluid impermeable membrane that at least partially defines a central fluid delivery lumen extending from a proximal end of the drive shaft toward a distal end portion of the drive shaft, the central fluid delivery lumen being coaxial with a longitudinal axis of the drive shaft;
an abrasive element mounted to the distal end portion of the drive shaft and extending around less than half of a circumference of the drive shaft, wherein the abrasive element comprises an abrasive outer surface that is fixedly positioned relative to the drive shaft;
a fluid inflatable distal counterweight fixedly positioned at a distal tip of the drive shaft such that the fluid inflatable distal counterweight rotates together with the abrasive element in response to rotation of the drive shaft, wherein the fluid inflatable distal counterweight is in fluid communication with the central fluid delivery lumen of the drive shaft such that the fluid inflatable distal counterweight is inflated in response to fluid transferring from the central fluid delivery lumen into an inflatable space of the fluid inflatable distal counterweight, the fluid inflatable distal counterweight being positioned distally of a distal end of the abrasive element and spaced axially apart from the abrasive element; and
a fluid inflatable proximal counterweight fixedly positioned on the drive shaft such that the fluid inflatable proximal counterweight rotates together with the abrasive element in response to rotation of the drive shaft, wherein the fluid inflatable proximal counterweight is in fluid communication with the central fluid delivery lumen of the drive shaft such that the fluid inflatable proximal counterweight is inflated in response to fluid transferring from the central fluid delivery lumen into an inflatable space of the fluid inflatable proximal counterweight, the fluid inflatable proximal counterweight being positioned proximally of a proximal end of the abrasive element and spaced axially apart from the abrasive element;
wherein a center of mass of each of the fluid inflatable distal counterweight and the fluid inflatable proximal counterweight is offset from the longitudinal axis of the drive shaft in a first direction while the center of mass of the abrasive element is offset from the longitudinal axis of the drive shaft in a second opposite direction.

2. The device of claim 1, wherein the fluid inflatable distal counterweight includes a flexible outer wall comprising at least one outflow opening configured to output fluid flow from the inflatable space of the fluid inflatable distal counterweight during rotation of the fluid inflatable distal counterweight.

3. The device of claim 2, wherein the fluid inflatable proximal counterweight includes a flexible outer wall comprising at least one outflow opening configured to output fluid flow from the inflatable space of the fluid inflatable proximal counterweight during rotation of the fluid inflatable proximal counterweight.

4. The device of claim 3, wherein the at least one outflow opening through the flexible outer wall of the fluid inflatable distal counterweight is located such that an axis of the at least one outflow opening forms an angle of at least about seventy five (75) degrees with the longitudinal axis of the drive shaft when the fluid inflatable distal counterweight is inflated.

5. The device of claim 4, wherein the at least one outflow opening of the fluid inflatable distal counterweight is configured to output fluid flow during rotation of the fluid inflatable distal counterweight for forming a fluid bearing between the outer wall of the fluid inflatable distal counterweight and a wall of a body vessel.

6. The device of claim 4, wherein the at least one outflow opening through the flexible outer wall of the fluid inflatable proximal counterweight is located such that an axis of the at least one outflow opening forms an angle of at least about seventy five (75) degrees with the longitudinal axis of the drive shaft when the fluid inflatable proximal counterweight is inflated.

7. The device of claim 6, wherein the at least one outflow opening of the fluid inflatable proximal counterweight is configured to output fluid flow during rotation of the fluid inflatable proximal counterweight for forming a fluid bearing between the outer wall of the fluid inflatable proximal counterweight and a wall of a body vessel.

8. The device of claim 1, wherein the fluid inflatable distal counterweight is spaced axially apart from the abrasive element by a distal separation distance, the fluid inflatable proximal counterweight is spaced axially apart from the abrasive element by a proximal separation distance, wherein the distal separation distance and the proximal separation distance are greater than an overall axial length of the abrasive element.

9. The device of claim 1, wherein the fluid inflatable distal counterweight is spaced axially apart from the abrasive element by a distal separation distance, the fluid inflatable proximal counterweight is spaced axially apart from the abrasive element by a proximal separation distance, wherein the distal separation distance is substantially equal to the proximal separation distance.

10. The device of claim 1, wherein the central fluid delivery lumen of the drive shaft extends to a distal port at a distal-most tip of the drive shaft, the distal port being configured to slidably receive a guide wire.

11. A rotational atherectomy device for removing a stenotic lesion from a body vessel, the device comprising:
a rotatable, flexible drive shaft comprising a torque transmitting coil and a central fluid delivery lumen configured to deliver fluid from a proximal end of the drive shaft to a distal end portion of the drive shaft;
an abrasive element mounted to the distal end portion of the drive shaft and extending around less than half of a circumference of the drive shaft, wherein the abrasive element comprises an abrasive outer surface that is fixedly positioned relative to the drive shaft;
a fluid inflatable distal counterweight fixedly positioned on the drive shaft distally of the abrasive element such that fluid inflatable distal counterweight is spaced axially apart from the abrasive element by a distal separation distance, the fluid inflatable distal counterweight having a distal end and a proximal end that are both affixed to the drive shaft such that the fluid inflatable distal counterweight rotates together with the abrasive element in response to rotation of the drive shaft, wherein the fluid inflatable distal counterweight is in fluid communication with the central fluid delivery lumen of the drive shaft; and a fluid inflatable proximal counterweight fixedly positioned on the drive shaft proximally of the abrasive element such that fluid inflatable proximal counterweight is spaced axially apart from the abrasive element by a proximal separation distance, the fluid inflatable proximal counterweight having a distal end and a proximal end that are both affixed to the drive shaft such that the fluid inflatable proximal counterweight rotates together with the abrasive element in response to rotation of the drive shaft, wherein the fluid inflatable proximal counterweight is in fluid communication with the central fluid delivery lumen of the drive shaft;

wherein a center of mass of each of the fluid inflatable distal counterweight and the fluid inflatable proximal counterweight is offset from the longitudinal axis of the drive shaft in a first direction while the center of mass of the abrasive element is offset from the longitudinal axis of the drive shaft in a second opposite direction.

12. The device of claim 11, wherein the inflatable space within the fluid inflatable distal counterweight extends around less that the entire circumference of the drive shaft so that, when the fluid inflatable distal counterweight is inflated with fluid, the center of mass of the fluid inflatable distal counterweight is offset from the longitudinal axis of the drive shaft in said first direction.

13. The device of claim 12, wherein the inflatable space within the fluid inflatable proximal counterweight extends around less that the entire circumference of the drive shaft so that, when the fluid inflatable proximal counterweight is inflated with fluid, the center of mass of the fluid inflatable proximal counterweight is offset from the longitudinal axis of the drive shaft in said first direction.

14. The device of claim 11, wherein the distal separation distance and the proximal separation distance are greater than an overall axial length of the abrasive element.

15. The device of claim 11, wherein the distal separation distance is substantially equal to the proximal separation distance.

16. The device of claim 11, wherein the fluid inflatable distal counterweight includes a flexible outer wall comprising at least one outflow opening configured to output fluid flow from the inflatable space of the fluid inflatable distal counterweight during rotation of the fluid inflatable distal counterweight.

17. The device of claim 16, wherein the at least one outflow opening of the fluid inflatable distal counterweight is configured to output fluid flow during rotation of the fluid inflatable distal counterweight for forming a fluid bearing between the outer wall of the fluid inflatable distal counterweight and a wall of a body vessel.

18. The device of claim 16, wherein the fluid inflatable proximal counterweight includes a flexible outer wall comprising at least one outflow opening configured to output fluid flow from the inflatable space of the fluid inflatable proximal counterweight during rotation of the fluid inflatable proximal counterweight.

19. The device of claim 18, wherein the at least one outflow opening of the fluid inflatable proximal counterweight is configured to output fluid flow during rotation of the fluid inflatable proximal counterweight for forming a fluid bearing between the outer wall of the fluid inflatable proximal counterweight and a wall of a body vessel.

20. The device of claim 11, wherein the central fluid delivery lumen of the drive shaft extends to a distal port at a distal-most tip of the drive shaft, the distal port being configured to slidably receive a guide wire.

* * * * *